(12) United States Patent
Bousquet et al.

(10) Patent No.: US 9,303,019 B2
(45) Date of Patent: Apr. 5, 2016

(54) AMINO-PYRROLINE DERIVATIVES, AND USE THEREOF IN THE PREVENTION AND/OR TREATMENT OF METABOLIC SYNDROME

(75) Inventors: Pascal Bousquet, Strasbourg (FR); Jean Daniel Ehrhardt, Kleinfrankenheim (FR); Lyne Fellmann, Behlenheim (FR); Vincent Gasparik, Chaumont en Vexin (FR); Hugues Greney, Strasboug (FR); Mohamed Hadjeri, Villefontaine (FR); Andre Mann, Ostwald (FR); Nathalie Niederhoffer, Uttenheim (FR); Stephan Schann, Illkirch (FR)

(73) Assignee: UNIVERSITE DE STRASBOURG, STRASBOURG (FR)

(*) Notice: Subject to any disclaimer, the term of this patent is extended or adjusted under 35 U.S.C. 154(b) by 0 days.

(21) Appl. No.: 14/112,631

(22) PCT Filed: Apr. 17, 2012

(86) PCT No.: PCT/FR2012/050835
§ 371 (c)(1),
(2), (4) Date: Oct. 18, 2013

(87) PCT Pub. No.: WO2012/143660
PCT Pub. Date: Oct. 26, 2012

(65) Prior Publication Data
US 2014/0045910 A1 Feb. 13, 2014

(51) Int. Cl.
*C07D 207/22* (2006.01)
*C07D 403/04* (2006.01)

(52) U.S. Cl.
CPC ............ *C07D 403/04* (2013.01); *C07D 207/22* (2013.01)

(58) Field of Classification Search
CPC .......................... C07D 207/22; C07D 403/04
See application file for complete search history.

(56) References Cited

U.S. PATENT DOCUMENTS

| 3,563,994 A | 2/1971 | Wollweber etal. |
| 4,533,739 A | 8/1985 | Pitzele et al. |
| 4,579,951 A | 4/1986 | Pitzele et al. |

FOREIGN PATENT DOCUMENTS

| WO | WO 2011/044229 | 4/2011 |
| WO | WO 2011/050030 | 4/2011 |

OTHER PUBLICATIONS

Bousquet et al., Annals of the New York Academy of Sciences (2003), 1009, 228-233.*
Sy et al. Journal of Hypertension (2008), 26(5), 1025-1032.*
Remko Bioorganic & Medicinal Chemistry (2006), 14(6), 1715-1728.*
Hershenson, F. et al. "Synthesis and Antihypertensive Activity of 2-Arylamino-1-azacycloalkenes" *Journal of Medicinal Chemistry*, 1971, pp. 907-909, vol. 14, No. 10.
De Jong, A. et al. "Relationships Between Structure and α-Adrenergic Receptor Affinity of Clonidine and Some Related Cyclic Amidines" *European Journal of Pharmacology*, 1981, pp. 175-188, vol. 69.
Urosevic, D. et al. "LNP 906, the first high-affinity photoaffinity ligand selective for $I_1$ imidazoline receptors" *British Journal of Pharmacology*, 2004, pp. 609-617, vol. 142.
Van Zwieten, P.A. "Antihypertensive drugs interacting with central imidazoline ($I_1$)-receptors" *Expert Opinion on Investigational Drugs*, Nov. 1998, pp. 1781-1793, vol. 7, No. 11.
Written Opinion in International Application No. PCT/FR2012/050835, Jun. 21, 2012, pp. 1-9.
Gasparik, V., et al., "Synthesis and Biological Evaluation of 2-Aryliminopyrrolidines as Selective Ligands for $I_1$ Imidazoline Receptors: Discovery of New Sympatho-Inhibitory Hypotensive Agents with Potential Beneficial Effects in Metabolic Syndrome," *Journal of Medicinal Chemistry*, 2015, vol. 58, pp. 878-887.
Greney, H., et al., "[$^{125}$I]2-(2-Chloro-4-iodo-phenylamino)-5-methyl-pyrroline (LNP 911), a High-Affinity Radioligand Selective for $I_1$ Imidazoline Receptors," *Molecular Pharmacology*, 2002, vol. 62, No. 1, pp. 181-191.
Schann, S., et al., "Methylation of imidazoline related compounds leads to loss of $\alpha_2$-adrenoceptor affinity. Synthesis and biological evaluation of selective $I_1$ imidazoline receptor ligands," *Bioorganic & Medicinal Chemistry*, 2012, vol. 20, pp. 4710-4715.
Wu, Y. et al. "Analeptics. 1-Formimidoylindolines" *Journal of Medicinal Chemistry*, 1970, pp. 975-977, vol. 13, No. 5.

* cited by examiner

*Primary Examiner* — Nyeemah A Grazier
(74) *Attorney, Agent, or Firm* — Saliwanchik, Lloyd & Eisenschenk

(57) ABSTRACT

Novel amino-pyrrolinic derivatives, their pharmacologically acceptable salts and use thereof in the prevention and/or treatment of metabolic syndrome.

19 Claims, 12 Drawing Sheets

FIGURE 1
Fig. 1A :
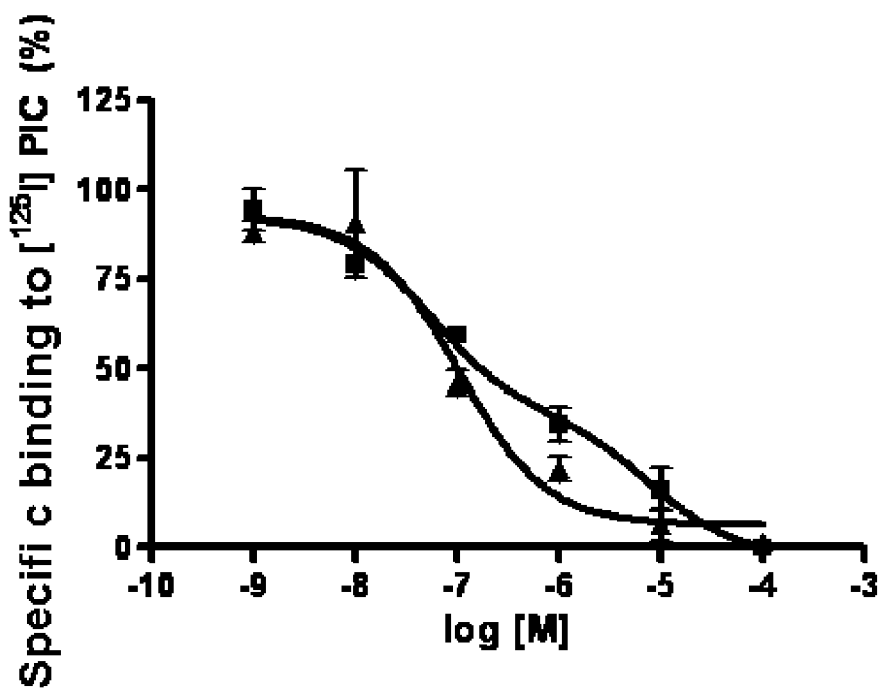
Fig. 1B
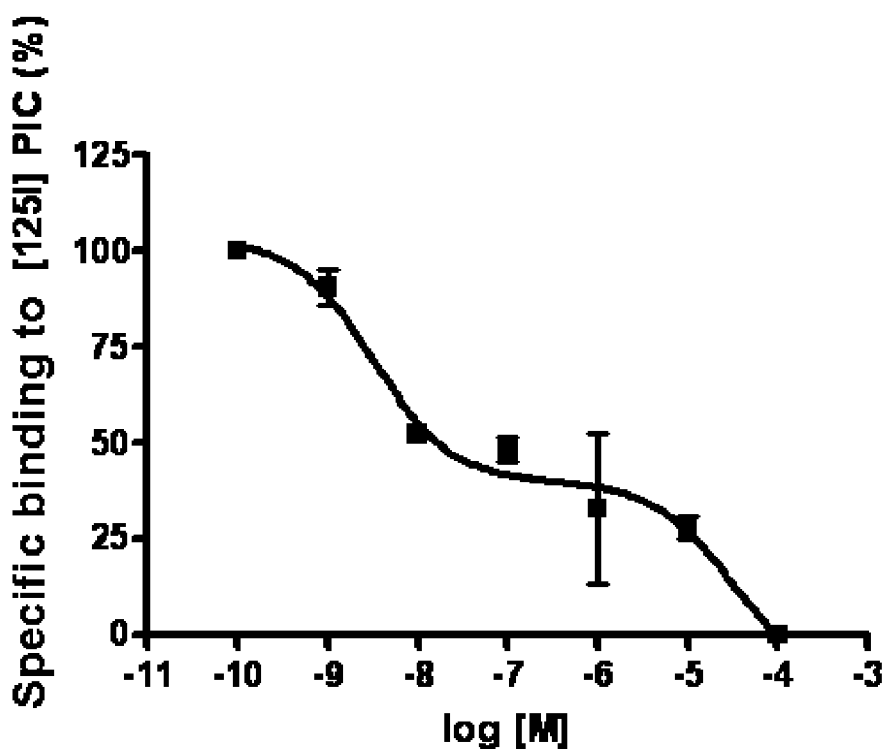

FIGURE 3

| Receptor and tested transporter | Concentration of compound 1 (M) | Displacement (%) |
|---|---|---|
| Adenosine $A_1$ receptor (human) | 1.0E-07 | 10 |
| | 1.0E-05 | -2 |
| Adenosine $A_{2A}$ receptor (human) | 1.0E-07 | 3 |
| | 1.0E-05 | -11 |
| $\alpha_1$-adrenergic receptor | 1.0E-07 | -1 |
| | 1.0E-05 | 34 |
| $\beta_1$-adrenergic receptor | 1.0E-07 | 5 |
| | 1.0E-05 | -4 |
| $\beta_2$-adrenergic receptor | 1.0E-07 | -4 |
| | 1.0E-05 | -5 |
| Angiotensin $AT_1$ receptor | 1.0E-07 | 8 |
| | 1.0E-05 | -3 |
| Benzodiazepine receptor (central) | 1.0E-07 | -2 |
| | 1.0E-05 | 6 |
| Bradykinin $B_2$ receptor | 1.0E-07 | -7 |
| | 1.0E-05 | -13 |
| CGRP (human) | 1.0E-07 | -12 |
| | 1.0E-05 | -12 |
| Cannabinoid $CB_1$ receptor (human) | 1.0E-07 | -4 |
| | 1.0E-05 | 1 |
| Cannabinoid $CB_2$ receptor (human) | 1.0E-07 | 23 |
| | 1.0E-05 | 13 |
| $CCK_1$ receptor (human) | 1.0E-07 | 4 |
| | 1.0E-05 | 8 |
| Dopamine $D_1$ receptor | 1.0E-07 | 4 |
| | 1.0E-05 | -7 |
| Dopamine $D_{2S}$ receptor (human) | 1.0E-07 | -41 |
| | 1.0E-05 | 36 |
| Dopamine $D_3$ receptor (human) | 1.0E-07 | -4 |
| | 1.0E-05 | 18 |
| Dopamine $D_{4.4}$ (receptor (human) | 1.0E-07 | 7 |
| | 1.0E-05 | 18 |
| Dopamine $D_5$ receptor (humain) | 1.0E-07 | -4 |
| | 1.0E-05 | 4 |
| Endothelin $ET_A$ receptor (human) | 1.0E-07 | 12 |
| | 1.0E-05 | 19 |
| Endothelin $ET_B$ receptor (human) | 1.0E-07 | 7 |
| | 1.0E-05 | 1 |
| GABA receptor | 1.0E-07 | 5 |
| | 1.0E-05 | -4 |
| AMPA receptor | 1.0E-07 | 10 |
| | 1.0E-05 | 11 |

Figure 3 (Cont.)

| Receptor and tested transporter | Concentration of compound 1 (M) | Displacement (%) |
|---|---|---|
| Kainate receptor | 1.0E-07 | 12 |
|  | 1.0E-05 | 16 |
| NMDA receptor | 1.0E-07 | 5 |
|  | 1.0E-05 | 6 |
| Récepteur $I_2$ receptor | 1.0E-07 | 17 |
|  | 1.0E-05 | 89 |
| Leukotriene $LTB_4$ receptor (human) | 1.0E-07 | 20 |
|  | 1.0E-05 | 10 |
| Muscarinic $M_1$ receptor (human) | 1.0E-07 | 0 |
|  | 1.0E-05 | 64 |
| Muscarinic $M_2$ receptor (human) | 1.0E-07 | 13 |
|  | 1.0E-05 | 50 |
| Muscarinic $M_3$ receptor (human) | 1.0E-07 | 3 |
|  | 1.0E-05 | 56 |
| Muscarinic $M_4$ receptor (humain) | 1.0E-07 | -17 |
|  | 1.0E-05 | 78 |
| Neurokinin $NK_1$ receptor (human) | 1.0E-07 | -7 |
|  | 1.0E-05 | -4 |
| Neurokinin $NK_2$ receptor (human) | 1.0E-07 | -7 |
|  | 1.0E-05 | 8 |
| Neuropeptide Y receptor | 1.0E-07 | 9 |
|  | 1.0E-05 | 20 |
| Nicotinic receptor (neuronal) | 1.0E-07 | -3 |
|  | 1.0E-05 | -3 |
| $\delta_2$ opioid receptor (human) | 1.0E-07 | -12 |
|  | 1.0E-05 | 8 |
| κ opioid receptor (human) | 1.0E-07 | 13 |
|  | 1.0E-05 | 27 |
| μ opioid receptor (human) | 1.0E-07 | 6 |
|  | 1.0E-05 | 14 |
| Thromboxane $A_2$ receptor (human) | 1.0E-07 | 5 |
|  | 1.0E-05 | 5 |
| Serotonin $5HT_{1B}$ receptor (human) | 1.0 -07 | -15 |
|  | 1.0E-05 | 7 |
| Serotonin $5HT_3$ receptor (human) | 1.0E-07 | -11 |
|  | 1.0E-05 | -3 |
| Serotonin $5HT_4$ receptor (human) | 1.0E-07 | -2 |
|  | 1.0E-05 | 8 |
| $\sigma_1$ receptor (human) | 1.0E-07 | 45 |
|  | 1.0E-05 | 95 |
| $\sigma_2$ receptor | 1.0E-07 | 1 |
|  | 1.0E-05 | 69 |
| oestrogen α receptor (human) | 1.0E-07 | 6 |
|  | 1.0E-05 | 6 |
| Progesterone receptor (human) | 1.0E-07 | 16 |

Figure 3 (Cont.)

| Receptor and tested transporter | Concentration of compound 1 (M) | Displacement (%) |
|---|---|---|
| | 1.0E-05 | 1 |
| Androgen receptor (human) | 1.0E-07 | -2 |
| | 1.0E-05 | -4 |
| L-type $Ca^{2+}$ channel (DHP site) | 1.0E-07 | 1 |
| | 1.0E-05 | 21 |
| L-type $Ca^{2+}$ channel (diltiazem site) | 1.0E-0 | -8 |
| | 1.0E-05 | 38 |
| L-type $Ca^{2+}$ channel (verapamil site) | 1.0E-07 | -1 |
| | 1.0E-05 | 14 |
| $K^+_{ATP}$ channel | 1.0E-07 | 0 |
| | 1.0E-05 | 11 |
| $K^+_V$ channel | 1.0E-07 | -22 |
| | 1.0E-05 | 2 |
| $SK^+_{Ca}$ channel | 1.0E-07 | -12 |
| | 1.0E-05 | -3 |
| $Na^+$ channel (site 2) | 1.0E-07 | 8 |
| | 1.0E-05 | 27 |
| Noradrenaline transporter (human) | 1.0E-07 | 8 |
| | 1.0E-05 | 12 |
| Dopamine transporter (human) | 1.0E-07 | -2 |
| | 1.0E-05 | 9 |
| Cholinergic transporter (human) | 1.0E-07 | 10 |
| | 1.0E-05 | 17 |
| Serotonin transporter (human) | 1.0E-07 | -16 |
| | 1.0E-05 | 9 |
| Tested enzyme | Concentration of tested compound 1 | Displacement % |
| Phospholipase $A_2$ | 1.0E-07 | 15 |
| | 1.0E-05 | 21 |
| $COX_1$ (human) | 1.0E-07 | -22 |
| | 1.0E-05 | -22 |
| $COX_2$ (human) | 1.0E-07 | 8 |
| | 1.0E-05 | -4 |
| 15-LipOxygenase | 1.0E-07 | 7 |
| | 1.0E-05 | 0 |
| iNOS | 1.0E-07 | -4 |
| | 1.0E-05 | -3 |
| Constitutive NOS | 1.0E-07 | -14 |
| | 1.0E-05 | 2 |
| Phosphodiesterase 1 | 1.0E-07 | 0 |
| | 1.0E-05 | 9 |
| Phosphodiesterase 2 (human) | 1.0E-07 | 19 |
| | 1.0E-05 | -3 |
| Phosphodiesterase 3 (human) | 1.0E-07 | -2 |
| | 1.0E-05 | -2 |
| Phosphodiesterase 4 (human) | 1.0E-07 | 2 |

Figure 3 (Cont.)

| Receptor and tested transporter | Concentration of compound 1 (M) | Displacement (%) |
|---|---|---|
| | 1.0E-05 | 2 |
| Phosphodiesterase 5 (human) | 1.0E-07 | -3 |
| | 1.0E-05 | -21 |
| ACE (human) | 1.0E-07 | -4 |
| | 1.0E-05 | 7 |
| Adenylate cyclase (stimulated) | 1.0E-07 | 2 |
| | 1.0E-05 | -5 |
| Guanylate cyclase (stimulated) | 1.0E-07 | -9 |
| | 1.0E-05 | -21 |
| PKC | 1.0E-07 | 10 |
| | 1.0E-05 | 13 |
| Phospholipase C | 1.0E-07 | -3 |
| | 1.0E-05 | 3 |
| Acetylcholinesterase (human) | 1.0E-07 | 2 |
| | 1.0E-05 | 2 |
| MonoAmineOxidase-A | 1.0E-07 | 0 |
| | 1.0E-05 | 4 |
| MonoAmineOxidase-B | 1.0E-07 | 9 |
| | 1.0E-05 | 7 |
| ATPase | 1.0E-07 | -2 |
| | 1.0E-05 | 1 |

FIGURE 9

Pharmacological effects of compounds 1-27 on mean arterial pressure (MAP) and heart rate (HR) in anesthetized normotensive rats

| | Intravenous route | | | Intracisternal route | | |
|---|---|---|---|---|---|---|
| Compounds | Dose (mg/kg) | Max Δ MAP (% var) | Max Δ HR (% var) | Dose (mg/kg) | Max Δ MAP (% var) | Max Δ HR (% var) |
| 1 | 3 | -30 | -18 | 0.3 | -30 | -33 |
| 2 | 3 | -38 | - | 0.3 | -37 | - |
| 3 | 10 | -5 NS | -4 | 0.3 | NA | NA |
| 4 | 10 | -28 | -20 | 0.3 | -25 | -30 |
| 5 | 10 | -37 | -20 | 0.3 | -32 | -29 |
| 6 | 10 | -25 | -18 | 0.3 | -20 | -25 |
| 7 | 3 | -35 | -22 | 0.3 | -30 | -30 |
| 8 | 10 | -10 | -6 | 0.3 | NA | NA |
| 9 | 10 | -12 | -5 | 0.3 | NA | NA |
| 10 | 10 | -42 | - | 0.3 | -40 | - |
| 11 | 10 | -32 | - | 0.3 | -25 | - |
| 12 | 10 | -50 | - | - | - | - |
| 13 | 10 | -8 NS | | 0.3 | NA | NA |
| 14 | 10 | -9 NS | -6 | 0.3 | NA | NA |
| 15 | 10 | -7 NS | -7 | 0.3 | NA | NA |
| 16 | 10 | -6 NS | -8 | 0.3 | NA | NA |
| 17 | 10 | -7 NS | -6 | 0.3 | NA | NA |
| 18 | 10 | -8 NS | -4 | 0.3 | NA | NA |
| 19 | 10 | -9 NS | -3 | 0.3 | NA | NA |
| 20 | 10 | -6 NS | -7 | 0.3 | NA | NA |
| 21 | 3 | -26 | -20 | 0.3 | -25 | -31 |
| 22 | 10 | -8 NS | -4 | 0.3 | NA | NA |
| 23 | 10 | -5 NS | -3 | 0.3 | NA | NA |
| 24 | 10 | -3 NS | -8 | 0.3 | NA | NA |
| 25 | 10 | -5 NS | -3 | 0.3 | NA | NA |
| 26 | 10 | -4 NS | -7 | 0.3 | NA | NA |
| 27 | 10 | -7 NS | -3 | 0.3 | NA | NA |

[#] NS non-significant; NA non-active

AMINO-PYRROLINE DERIVATIVES, AND USE THEREOF IN THE PREVENTION AND/OR TREATMENT OF METABOLIC SYNDROME

CROSS-REFERENCE TO RELATED APPLICATION

This application is the U.S. national stage application of International Patent Application No. PCT/FR2012/050835, filed Apr. 17, 2012.

The present invention concerns novel amino-pyrrolinic derivatives and the use thereof in the prevention and/or treatment of metabolic syndrome.

Metabolic syndrome, also called syndrome X or dysmetabolic syndrome, is a combination of cardiovascular symptoms, in particular arterial hypertension and metabolic symptoms (hypercholesterolemia, insulin resistance, glucose intolerance, abdominal obesity (Reaven, G. M. 1998. Banting lecture 1988; Role of insulin resistance in human disease. Diabetes 37:1595-1607). The combining of all these symptoms is unanimously recognized as forming a major cardiovascular and metabolic risk factor.

The complications of this metabolic syndrome are in particular atherosclerosis, coronary disease, kidney failure, heart failure, diabetes, obesity. The prevalence of this risk factor varies from country to country. Nevertheless it tends to emerge everywhere in the world in about 30% of the general population. Its rapid development is most important and raises major public health problems.

Current medication therapy of metabolic syndrome is formed of an association of drugs composed of medications each acting on only one element of metabolic syndrome among the 3 to 6 elements included therein: antihypertensive drugs (sometimes an association of several) in combination with hypoglycaemic drugs (sometimes an association of several) in combination with hypolipidemic drugs (sometimes an association of several).

These combinations generate numerous adverse effects and some e.g. statins are high-cost.

Although several studies have shown that metabolic syndrome is associated with sympathetic hyperactivity measured by an increase in Muscle Sympathetic Nerve Activity (MSNA) even in the absence of high blood pressure (Huggett R. J.; Burns J.; Mackintosh A. F.; Mary D. A. S. G. Sympathetic Neural Activation in Nondiabetic Metabolic Syndrome and Its Further Augmentation by Hypertension. *Hypertension*, 2004, 44:847-852), no currently available mediation able to inhibit the sympathetic system is proposed to treat metabolic syndrome and its consequences.

The imidazoline receptors (IRs) are involved in several biological regulatory systems. The chief system is regulation, by the sympathetic neural system, of high blood pressure (Bousquet, P.; Feldman, J. Drugs Acting on Imidazoline Receptors: a Review of their Pharmacology, their Use in Blood Pressure Control and their Potential Interest in Cardioprotection. *Drugs* 1999, 58, 799-812; Head, G. A.; Mayorov, D. N. Imidazoline Receptors, Novel Agents and Therapeutic Potential. *Cardiovasc. Hematol. Agents Med. Chem.* 2006, 4, 17-32).

They are also involved in other physiopathological functions such as insulin secretion (Chan, S. L. F. Clonidine-displacing Substance and its Putative Role in Control of Insulin Secretion: A Minireview. *Gen. Pharmacol.* 1998, 31, 525-529), the regulation of intraocular pressure (Chu, T. C.; R, S. R.; Ogidigben, M. J.; Potter, E. D. Potential Mechanisms of Moxonidine-induced Ocular Hypotension: Role of Norepinephrine. *J. Ocul. Pharmacol. Ther.* 1997, 13, 489-496) and heart rate control (Roegel, J. C.; de Jong, W.; Monassier, L.; Feldman, J.; Bousquet, P. Comparative Effects of Idazoxan, Prazocine and Yohimbine on Coronary Ligation-induced Arrhythmias in Spontaneously Hypertensive Rats. *J. Cardiovasc. Pharmacol.* 1996, 27, 226-234).

IRs are classified into three main sub-types $IR_1$, $IR_2$ and $IR_3$. The first sub-type $IR_1$ is located in the rostro-ventrolateral medulla (RVLM) of the brain stem and is involved in the central regulation of cardiovascular function.

$IR_1$ is sensitive to clonidine and to other compounds of imidazoline type but not to catecholamines and therefore differ from the $\alpha_2$-adrenergic receptors ($\alpha_2RA$).

Agmatine, <<clonidine displacing substances>> and harmane are endogenous ligands of $IR_1$.

$IR_2$ is insensitive to clonidine but sensitive to idazoxan. $IR_2$ are sub-divided into two sub-types depending on their affinity for amiloride (Tesson, F.; Prib-Buus, C.; Lemoine, A.; Pegorier, J. P.; Parini, A. A Subcellular Distribution of Imidazoline-Guanidinium Receptive Sites in Human and Rabbit Liver. Major Localization to the Mitochondrial Outer Membrane. *J. Biol. Chem.* 1991, 266, 155-160).

A third sub-type, $IR_3$, was added to the classification and is involved in insulin regulation (Englen, R. M.; Hudson, A. L.; Kendall, D. A.; Nutt, D. J.; Morgan, N. G.; Wilson, V. G.; Dillon, M. P. "Seeing Through a Glass Darkly": Casting Light on Imidazoline "I" Sites. *Trends Pharmacol. Sci.* 1998, 19, 381-390).

Clonidine is the leading compound of first generation antihypertensive drugs acting centrally. It binds both to $IR_1$ and to $\alpha_2AR$. Its side effects, sedation in particular, are clearly due to activation of $\alpha_2AR$ (De Sarro, G. B.; Ascioti, C.; Froio, F.; Libri, V.; Nistico, G. Evidence that Locus Coeruleus is the Site where Clonidine and Drugs Acing on $\alpha_1$- and $\alpha_2$-Adrenoceptors Affect Sleep and Arousal Mechanisms. *Br. J. Pharmacol.* 1987, 90, 675-685).

Drugs such as moxonidine and rilmedidine have selectivity for $IR_1$ compared with $\alpha_2$-AR since they have lower affinity for $\alpha_2$-AR and therefore cause fewer side effects in hypertensive patients.

Until recently, the lack of IR-selective hypotensive drugs has been a major curb for research into these receptors.

On the one hand hypotensive imidazolinic drugs such as clonidine and its analogues are all <<hybrid>> drugs since they bind both to $IR_1$ and to $\alpha_2AR$.

On the other hand, the few compounds that have been available up until now that are highly selective for $IR_1$ such as AGN192403 (Munk, S. A.; Lai, R. K.; Burke, J. E.; Arasasingham, P. N.; Kharlamb, A. B.; Manlapaz, C. A.; Padillo, E. U.; Wijono, M. K.; Hasson, D. W.; Wheeler, L. A.; Garst, M. E. Synthesis and Pharmacologic Evaluation of 2-endo-Amino-3-exo-isopropylbicyclo[2,2,1]heptane: A Potent Imidazoline$_1$ Receptor Specific Agent. *J. Med. Chem.* 1996, 39, 1193-1195), tracizoline and benazoline (Pigini, M.; Bousquet, P.; Carotti, A.; Dontenwill, M.; Giannella, M.; Moriconi, R.; Piergentili, A.; Quaglia, W.; Tayebati, S. K.; Brasili, L. Imidazoline Receptors: Qualitative Structure-Activity Relationships and Discovery of Tracizoline and Benazoline. Two Ligands with High Affinity and Unprecedented Selectivity. *Bioorg. Med. Chem.* 1997, 5, 833-841) do not modify high blood pressure or only scarcely.

In addition, there exist several compounds selective for $IR_1$ compared with $a_2$-AR but not compared with $IR_2$ such as S23757 (Anastasiadou, M.; Danoun, S.; Crane, L.; Baziard-Mouysset, G.; Payard, M.; Caignard, D.-H.; Rettori, M.-C.; Renard, P. Synthesis and Pharmacological Evaluation of Imidazoline Sites I and $I_2$ Selective Ligands. *Bioorg. Med. Chem.*

2001, 9, 585-592) and PMS 952 (Ye, H. F.; Dive, G.; Dehareng, D.; Heymans, F.; Godfroi, J. J. Structure-Activity Relationship on Adrenoreceptors and Imidazoline-Preferring Binding Sites ($I_{1,2}$-PBS). Part 1: Weak Intramolecular H-bond and Conformational Flexibility in a New $I_1$-PBS-Selective Imidazoline Analogue, trans1-(4'-5'-Dihydro-1'H-imidazol-2'-yl)methyl-2-hydroxyindane (PMS 952). *Bioorg. Med. Chem.* 2000, 8, 1861-1869).

Recently, compounds selective for $IR_1$, LNP 911 and LNP 906 which are aminopyrrolines, contrary to the other compounds described above having nanomolar affinities for the $IR_1$ receptor, have respectively been developed as radioligand and photoaffinity radioligand (Greney, H.; Urosevic, D.; Schann, S.; Dupuy, L.; Bruban, V.; Ehrhardt, J.-D.; Bousquet, P.; Dontenwill, M. [$^{125}$I]2-(2-Chloro-4-iodo-phenylamino)-5-methyl-pyrroline (LNP911), a High-Affinity Radioligand Selective for $I_1$ Imidazoline Receptors. *Mol. Pharmacol.* 2002, 62, 181-191) but do not have any hypotensive effect. LNP 911 behaves more as an antagonist whilst LNP 906 which is a photoactivatable ligand cannot be used in in vivo experiments.

As a result, there is a need to develop compounds which are selective for $IR_1$, so as to avoid side effects, which still have hypotensive activity and which are able to be used in monotherapy for metabolic syndrome.

It is one of the objectives of the present invention to provide compounds selective for $IR_1$ which therefore do not or only scarcely interact with $\alpha_2AR$ and $IR_2$. In addition, the compounds are agonists of $IR_1$.

A further objective of the invention is to provide medications active in metabolic syndrome which can be used in monotherapy and do not have the side effects of current drugs.

A further objective of the invention is to provide pharmaceutical compositions comprising said active medications.

The present invention therefore concerns compounds of following general formula (I):

(I)

wherein:
a) either R12 represents H, a straight-chain or branched C1 to C8 alkyl, C2-C8 alkene, C1-C8 acyl, a C1-C8 sulfonylalkyl, and
R1, R2, R3, R4 and R5 independently of each other being:
  H, a halogen, a straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, $CO_2H$, $CO_2R'$ where R' is a straight-chain or branched C1-C8 alkyl, or a C3-C6 cycloalkyl,
R1 and R2 and/or R2 and R3 and/or R3 and R4 and/or R4 and R5 possibly also together forming a C4-C6 ring,
R6, R7, R8, R9, R10 and R11 independently of each other being:
  H, a straight-chain or branched C1-C8 alkyl, C2-C8 alkene, C3-C6 cycloalkyl, C1-C5 perfluoroalkyl b) or R12 represents $CH(R13)(CH_2)_n$ and forms a C5-C7 ring with R5 which represents $CH_2$, n equalling 1 or 2, R13 representing H or $CH_3$, and R1 to R4 and R6 to R11 are such as defined above,
and the pharmacologically acceptable salts thereof,
with the exception of compounds of formula (I) in which:
  one of R10 or R11 represents a methyl and the other represents H, and one of R1 or R5 represents a cyclopropyl and the other represents H,
  one of R8 or R9 represents a methyl the other representing H, and one of R1 or R5 represents a cyclopropyl the other representing H,
  one of R10 or R11 represents a methyl the other representing H, and one of R1 or R5 represents a chlorine the other representing H,
  one of R10 or R11 represents a methyl and the other represents H, and one of R1 or R5 represents a chlorine the other representing H, and R3 represents iodine.

In one advantageous embodiment, when R12 represents H, R1 and R2 are not hydrogens, R6, R7, R9 and R11 are hydrogens, and R8 and R10 are chosen from the group consisting of a hydrogen and a straight-chain or branched C1 to C5 alkyl, at least one thereof being a straight-chain or branched C1 to C5 alkyl. Preferably R1 and R2 are chosen from the group consisting of a halogen, a straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, —OH, —SH, a primary, secondary or tertiary amine, —CN, —$CO_2H$, —$CO_2R'$ where R' is a straight-chain or branched C1-C8 alkyl, and a C3-C6 cycloalkyl, or together form a C5 ring. In one preferred embodiment, R3 is a hydrogen, in particular when R1 and R2 together form a C5 ring.

Preferably, R3, R4 and R5 independently of each represent H, a halogen, a straight-chain or branched C1 to C8 alkyl, C2-C8 alkene, a straight-chain or branched C1 to C8 alkoxy, C1-C5 perfluoroalkyl, C1-C8 acyl, —OH, —SH, a primary, secondary or tertiary amine, —CN, —$CO_2H$ or —$CO_2R'$ where R' is a straight-chain or branched C1-C8 alkyl, preferably they are chosen from among H, a halogen, a straight-chain or branched C1-C3 alkyl, a straight-chain or branched C1-C3 alkoxy, a C1-C3 perfluoroalkyl, a C1-C3 acyl, OH, SH, a primary, secondary or tertiary amine, CN, $CO_2H$ or $CO_2R'$ where R' is a straight-chain or branched C1-C3 alkyl. On one further preferred embodiment R3, R4 and R5 are hydrogens.

Preferably, R1 and R2 are chosen from the group consisting of a halogen, a straight-chain or branched C1 to C8 alkyl, straight-chain or branched C1 to C8 alkoxy, C1-C5 perfluoroalkyl, C1-C8 alkyl, OH, SH, a primary, secondary or tertiary amine, CN, $CO_2H$ and $CO_2R'$ where R' is a straight-chain or branched C1-C8 alkyl, or together form a C5 ring. More particularly R1 and R2 are chosen from the group consisting of a halogen, a straight-chain or branched C1-C3 alkyl, straight-chain or branched C1 to C3 alkoxy, C1-C3 perfluoroalkyl and C1-C3 acyl, or together form a C5 ring.

Preferably R8 and R10 are chosen from the group consisting of a hydrogen and a methyl or isobutyl so that one thereof is a hydrogen and the other a methyl or isobutyl, preferably a methyl.

In another advantageous embodiment, when R12 is $CH(R13)(CH_2)$ and forms a C5 ring with R5, R13 represents a methyl.

In another advantageous embodiment, when R12 is $CH(R13)(CH_2)$ and forms a C5 ring with R5, R1 is not a hydrogen.

In one advantageous embodiment, when R12 is CH(R13)(CH$_2$) and forms a C5 ring with R5, R13 represents a methyl and/or R1 is not a hydrogen. In other words, when R13 is a hydrogen then R1 is not a hydrogen, or at least one from R1 and R13 is not a hydrogen.

Preferably, R1, R2, R3 and R4 independently of each other represent a hydrogen, halogen, straight-chain or branched C1-C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, CO$_2$H, CO$_2$R' where R' is a straight-chain or branched C1-C8 alkyl, and a C3-C6 cycloalkyl. In particular, R1, R2, R3 and R4 are chosen from the grouped consisting of a hydrogen, halogen, straight-chain or branched C1 to C8 alkyl, C2-C8 alkene, straight-chain or branched C1 to C8 alkoxy, a polyether chain, a C1-C5 perfluoroalkyl, C1-C8 acyl, OH, SH, a primary, secondary or tertiary amine, CN, CO$_2$H and CO$_2$R' where R' is a straight-chain or branched C1-C8 alkyl, further preferably from the group consisting of a halogen, a straight-chain or branched C1-C3 alkyl, straight-chain or branched C1 to C3 alkoxy, C1-C3 perfluoroalkyl and C1-C3 acyl. In one preferred embodiment, R1 is a hydrogen or a straight-chain or branched C1 to C3 alkyl, preferably a hydrogen or a methyl. In a further preferred embodiment R2, R3 and R4 are hydrogens.

Therefore the present invention particularly concerns compounds of general formula (I) wherein:
a) either R12 represents H, and
  R1 and R2 independently of each other are:
    a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, a C1-C5 perfluoroalkyl, C1-C8 acyl, OH, SH, a primary, secondary or tertiary amine, CN, CO$_2$H, CO$_2$R' where R' is a straight-chain or branched C1-C8 alkyl, or a C3-C6 cycloalkyl; or
  R1 and R2 together from a C5 ring,
  R3, R4 and R5 independently of each other are:
    a hydrogen, halogen, straight-chain or branched C1 to C8 alkyl, C2-C8 alkene, straight-chain or branched C1 to C8 alkoxy, C3 to C6 cycloalkyl, C5-C6 bicycloalkyl, a polyether chain, a C1-C5 perfluoroalkyl, C1-C8 acyl, OH, SH, a primary, secondary or tertiary amine, CN, CO$_2$H, CO$_2$R' where R' is a straight-chain or branched C1-C8 alkyl or a C3-C6 cycloalkyl;
  R6, R7, R9 and R11 are hydrogens;
  R8 and R10 are chosen from the group consisting of a hydrogen and C1 to C5 straight-chain or branched alkyl, at least one of the two being a straight-chain or branched C1 to C5 alkyl;
b) or R12 represents CH(R13)(CH$_2$) and forms a C5 ring with R5, R13 being H or CH$_3$;
  R1, R2, R3 and R4 are chosen from the group consisting of a hydrogen, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, a C1-C5 perfluoroalkyl, C1-C8 acyl, —OH, —SH, a primary, secondary or tertiary amine, —CN, —CO$_2$H, —CO$_2$R' where R' is a straight-chain or branched C1-C8 alkyl, and a C3-C6 cycloalkyl;
  R6, R7, R9 and R11 are hydrogens;
  R8 and R10 are chosen from the group consisting of a hydrogen and straight-chain or branched C1 to C5 alkyl, at least one of the two being a straight-chain or branched C1 to C5 alkyl,
  provided that at least one of R1 and R13 is not a hydrogen, and the pharmacologically acceptable salts thereof.

The carbons carrying R13 when it differs from H, or R6 and R7 when they differ from each other, or R8 if different from R9, and R10 if different from R11, are asymmetric and each of said carbons may therefore be of absolute configuration (R) or (S) or (R,S).

In the entire description, the following expressions always have the same meaning:

<<straight-chain or branched C1 to C8 alkyl>> designates a methyl, ethyl, n-propyl, n-butyl, n-pentyl, n-hexyl, n-heptyl or n-octyl and all their isomers namely isopropyl, isobutyl, sec-butyl and tert-butyl, isopentane (or 2-methylbutyl) or neopentane (or 2,2 dimethylpropyl), 2,2-dimethylbutane, 2,3-dimethylbutane, 2-methylpentane, 3-methylpentane, 2-methylhexane, 3-methylhexane, 2,2 dimethylpentane, 2,3-dimethylpentane, 2,4-dimethylpentane, 3,3-dimethylpentane, 3-ethylpentane, 2,2,3-trimethylbutane, 2-methylheptane, 3-dimethylheptane, 4-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane, 2,3,3-trimethylpentane, 2,3,4-trimethylpentane, 2-methyl-3-ethylpentane, 3-methyl-3-ethylpentane, tetramethylbutane.

The said alkyl may also be substituted in particular by an alcohol, a thiol, an ether, a halogen, a nitrile, a primary, secondary or tertiary amine;

<<C2-C8 alkene>> designates an ethylene, propene, butene, pentene, hexene, heptene or octene and all the isomers thereof.

The said alkene may also be substituted, in particular by an alcohol, a thiol, an ether, a halogen, a nitrile, a primary, secondary or tertiary amine;

<<C1-C8 acyl>> designates a C1-C8-C(O)— alkyl group whose alkyl is such as defined above;

<<C1-C8 sulfonylalkyl>> designates an S(O)$_2$O-alkyl group where the C1-C8 alkyl is such as defined above;

a halogen designates a bromium, chlorine, fluorine or iodine;

<<straight-chain or branched C1-C8 alkoxy>> designates an O-alkyl i.e. a straight-chain or branched C1-C8 alkyl having the same definition as above, linked by an oxygen to the molecule of formula (I).

The said alkoxy can also be substituted, in particular by an alcohol, a thiol, an ether, a halogen, a nitrile, a primary, secondary or tertiary amine;

<<C3-C6 cycloalkyl>> designates a cyclopropyl, cyclobutyl, cyclopentyl or cyclohexyl;

<<C5-C6 bicycloalkyl>> designates two C5 and/or C6 fused cycloalkyl rings;

The said cycloalkyls or bicycloalkyls can also be substituted, in particular by an alcohol, a thiol, an ether, a halogen, a nitrile, a primary, secondary or tertiary amine;

a polyether chain designates an O—(CH$_2$—CH$_2$—O)$_n$CH$_2$—CH$_2$—OR" chain, n
  varying from 0 to 9 and R" representing an alkyl or alkene or cycloalkyl such as defined above;

<<C1-C5 perfluoroalkyl>> designates a C1-C5 alkyl such as defined above in which all the hydrogens are fully substituted by a fluorine, for example CF$_3$, C$_2$F$_5$, C$_3$F$_7$, C$_4$F$_9$, C$_5$F$_{11}$, a primary, secondary or tertiary amine designates an —NR$_a$R$_b$ group where R$_a$ and R$_b$ independently of each other designate H, a straight-chain or branched C1-C6 alkyl, C3-C6 cycloalkyl, C1-C6 acyl.

When R12 represents CH(R13)(CH$_2$)$_n$ and forms a 5, 6 or 7C ring with R5 which represents CH$_2$, n equaling 0, 1 or 2, R13 representing H or CH$_3$, the following formulas I-1 to I-3 are obtained:

5C ring:

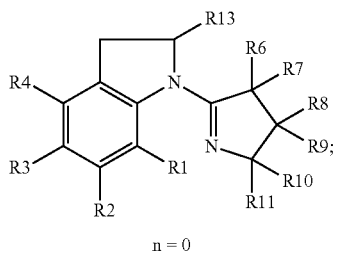

(I-1)

n = 0

6C ring:

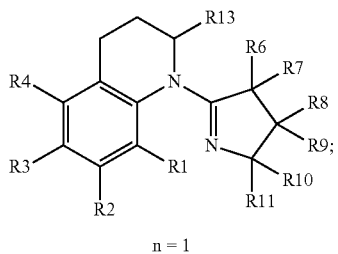

(I-2)

n = 1

7C ring:

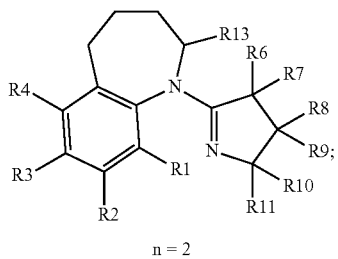

(I-3)

n = 2

In one preferred embodiment, the compounds are of formula I-1.

The expression <<pharmacologically acceptable salts>> means that the compounds of formula I defined above, when they have a radical representing an amine, may exist in the form of ammonium via reaction of an inorganic acid or organic acid on the amine.

Examples of inorganic acids allowing pharmacologically acceptable salts to be obtained include, without being limited thereto, hydrochloric acid, hydrobromic acid, nitric acid, carbonic acid, formic acid, monohydrogenocarbonic acid, phosphoric acid, monohydrogenophosphoric acid, dihydrogenophosphoric acid, perchloric acid, sulfuric acid, monohydrogenosulfuric acid, hydroiodic acid.

Examples of organic acids allowing pharmacologically acceptable salts to be obtained include, without being limited thereto, acetic acid, lactic acid, propionic acid, butyric acid, isobutyric acid, palmitic acid, maleic acid, glutamic acid, hydroxymaleic acid, malonic acid, benzoic acid, succinic acid, glycolic acid, suberic acid, fumaric acid, mandelic acid, phthalic acid, salicylic acid, benzenesulfonic acid, p-toluenesulfonic acid, citric acid, tartaric acid, methanesulfonic acid, hydroxynaphthoic acid.

The salts of amino acids such as arginates and their equivalents are also included as well as salts of organic acids such as glucuronic acid or galacturonic acid and their equivalents (see for example Berge et al <<Pharmaceutical Salts>>, *Journal of Pharmaceutical Science*, 1977, 66, 1-19).

Alkyl halides allowing pharmacologically acceptable salts to be obtained include, without being limited thereto, alkyl bromides, iodides, fluorides or chlorides in which the said alkyl residue is saturated or unsaturated, straight-chain or branched with 1 to 20 carbon atoms, or an O-cycloalkyl group with 3 to 8 carbon atoms.

When the compounds of formula I of the invention have a radical representing an acid or OH, in particular a phenol, they may exist in carboxylate, alcoholate or phenate form e.g. of sodium, potassium, lithium or ammonium by reaction of the acid, alcohol or phenol with a base for example such as sodium hydroxide, potash, lithium hydroxide, ammonia . . . .

Unexpectedly the inventors have found that the compounds of the invention through their original pyrroline structure are selective for the IR$_1$ imidazoline receptor compared with the α$_2$-adrenergic receptor, the ratio Ki(α$_2$AR)/Ki(IR$_1$) varying from 100 to over 10000.

The compounds of the invention are also selective for the IR$_1$ imidazoline receptor compared with the IR$_2$ imidazoline receptor, the ratio Ki(IR$_2$)/Ki(IR$_1$) being about 1000.

In addition, the compounds of the invention are also selective for the IR$_1$ imidazoline receptors compared with more than about fifty other potential targets, receptors or enzymes, in particular those given in the Table in FIG. 3.

Finally, to exhibit the desired therapeutic effect, the compounds of the invention are agonists of the IR$_1$ imidazoline receptor. This agonist effect can be measured using any method available to persons skilled in the art. In particular it can be assayed by measuring the hypotensive capability of the compounds.

In one advantageous embodiment, the present invention concerns compounds such as defined above, of general formula (I) in which:
  R1, R2, R3, R4 and R5 independently of each other represent:
    H, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, CO$_2$H, CO$_2$R' where R' is a straight-chain or branched C1-C8 alkyl, or a C3-C6 cycloalkyl,
  R1 and R2 and/or R2 and R3 and/or R3 and R4 and/or R4 and R5 possibly also together forming a C4-C6 ring.
  R6, R7, R8, R9, R10 and R11 independently of each other representing:
    H, a straight-chain or branched C1 to C8 alkyl, C2-C8 alkene, C3-C6 cycloalkyl
  R12 represents H, a straight-chain or branched C1 to C8 alkyl, C2-C8 alkene, C1-C8 acyl, C1-C8 sulfonylalkyl.

In one advantageous embodiment, the present invention concerns compounds such as defined above, of following general formula (Ia):

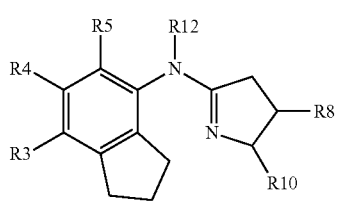

(Ia)

where R8 and R10 independently of each other represent H or a straight-chain or branched C1 to C5 alkyl, in particular CH$_3$, R3 to R5 are such as defined above and R12 represents H, a C1 to C6 straight-chain or branched alkyl, C2-C8 alkene, C1 to C8 acyl, C1 to C8 sulfonylalkyl.

Preferably, R12 is a hydrogen, and R8 and R10 are chosen from the group consisting of a hydrogen and straight-chain or branched C1 to C5 alkyl, at least one of the two being a straight-chain or branched C1 to C5 alkyl. More particularly, R8 and R10 are chosen from the group consisting of a hydrogen and a methyl or isobutyl so that one thereof is a hydrogen and the other a methyl or isobutyl, preferably a methyl. In one preferred embodiment, R3 is a hydrogen. In a further preferred embodiment, R3, R4 and R5 are hydrogens.

In another advantageous embodiment, the present invention concerns compounds such as defined above, of following general formula (Ia):

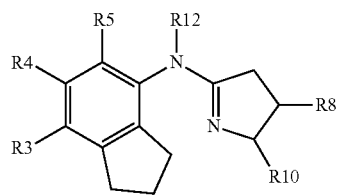

(Ia)

where

R3 and R12 are hydrogens,

R8 and R10 are chosen from the group consisting of a hydrogen and a straight-chain or branched C1 to C5 alkyl, at least one of the two being a straight-chain or branched C1 to C5 alkyl, and R4 and R5 are independently chosen from the group formed a hydrogen, a halogen, straight-chain or branched C1 to C3 alkyl, C1 to C3 straight-chain or branched alkoxy, C1-C3 perfluoroalkyl, C1-C3 acyl, OH, SH, a primary, secondary or tertiary amine, CN, CO$_2$H and CO$_2$R' where R' is a straight-chain or branched C1-C3alkyl, preferably from the group consisting of a halogen, straight-chain or branched C1 to C3 alkyl, straight-chain or branched C1 to C3 alkoxy, C1-C3 perfluoroalkyl and C1-C3 acyl.

Preferably, R4 and R5 are hydrogens.

In another advantageous embodiment, the present invention concerns compounds such as defined above of following general formula (Ib):

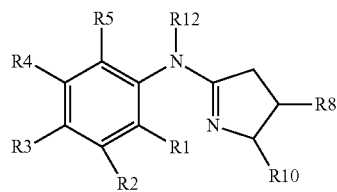

(Ib)

where R8 and R10 independently of each other represent H or C1-C5 straight-chain or branched alkyl, in particular CH$_3$, R1 and R2 independently of each other represent H, CH$_3$ or Cl, R3 to R5 are such as defined above and R12 represents H, a straight-chain or branched C1 to C8 alkyl, C2-C8 alkene, C1-C8 acyl, C1-C8 sulfonylalkyl.

Preferably, R12 is a hydrogen. Preferably, R8 and R10 are chosen from the group consisting of a hydrogen and straight-chain or branched C1 to C5 alkyl, at least one of the two being a straight-chain or branched C1 to C5 alkyl. More particularly, R8 and R10 are chosen from the group consisting of a hydrogen and a methyl or isobutyl so that one thereof is a hydrogen and the other a methyl or isobutyl, preferably a methyl. Preferably R1 and R2 independently of each other represent CH$_3$ or Cl. In particular R1 is a methyl and R2 is a methyl or chloride. In a further preferred embodiment R3, R4 and R5 are hydrogens.

In another advantageous embodiment the present invention concerns compounds such as defined above of following general formula (Ib):

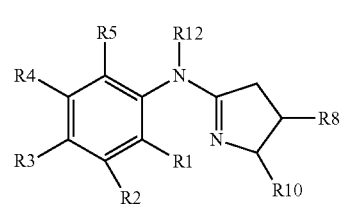

(Ib)

where

R12 is a hydrogen;

R8 and R10 are chosen from the group consisting of a hydrogen and straight-chain or branched C1 to C5 alkyl, at least one of the two being a straight-chain or branched C1 to C5 alkyl;

R1 and R2 are independently chosen from the group consisting of a halogen, straight-chain or branched C1 to C3 alkyl, straight-chain or branched C1 to C3 alkoxy, C1-C3 perfluoroalkyl and C1-C3 acyl; and R3, R4 and R5 are independently chosen from the group consisting of a hydrogen, a halogen, straight-chain or branched C1 to C3 alkyl, straight-chain or branched C1 to C3 alkoxy, C1-C3 perfluoroalkyl, C1-C3 acyl, OH, SH, a primary, secondary or tertiary amine, CN, CO$_2$H and CO$_2$R' where R' is a straight-chain or branched C1-C3 alkyl, preferably from the group consisting of a halogen, straight-chain or branched C1 to C3 alkyl, straight-chain or branched C1 to C3 alkoxy, C1-C3 perfluoroalkyl and C1-C3 acyl.

Preferably, R1 and R2 are independently chosen from the group consisting of a halogen and straight-chain or branched C1 to C3 alkyl. Further preferably R1 and R2 independently represent CH$_3$ or Cl.

Preferably R3, R4 and R5 are hydrogens.

In another advantageous embodiment, the present invention concerns compounds such as defined above, of following general formula (Ia-1):

(Ia-1)

where R3 and R8 are such as defined above. Preferably R8 is a straight-chain or branched C1 to C5 alkyl, in particular a methyl or isobutyl, preferably a methyl. Preferably R3 is a hydrogen.

In another advantageous embodiment, the present invention concerns compounds such as defined above, of following formula (Ib-1):

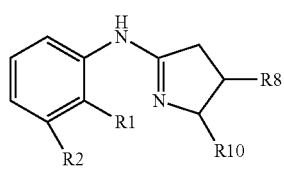
(Ib-1)

where R1, R2, R8 and R10 are such as defined above. Preferably R8 and R10 are chosen from the group consisting of a hydrogen and straight-chain or branched C to C5 alkyl, at least one of the two being a straight-chain or branched C1 to C5 alkyl. More particularly R8 and R10 are chosen from the group consisting of a hydrogen and a methyl or isobutyl so that one thereof is a hydrogen and the other a methyl or isobutyl, preferably a methyl. Preferably, R1 and R2 are chosen from the group consisting of a halogen, straight-chain or branched C1 to C8 alkyl, straight-chain or branched C1 to C8 alkoxy, C1-C5 perfluoroalkyl, C1-C8 acyl, OH, SH, a primary, secondary or tertiary amine, CN, $CO_2H$ and $CO_2R'$ where R' is a straight-chain or branched C1-C8 alkyl, or together form a C5 ring. More particularly R1 and R2 are chosen from the group consisting of a halogen, straight-chain or branched C to C3 alkyl, straight-chain or branched C to C3 alkoxy, C1-C3 perfluoroalkyl and C1-C3 acyl, or together form a C5 ring. Preferably R1 and R2 each independently represent $CH_3$ or Cl. In particular R1 is a methyl and R2 is a methyl or chloride.

In another advantageous embodiment the present invention concerns compounds such as defined above, chosen from among one of the following formulas:

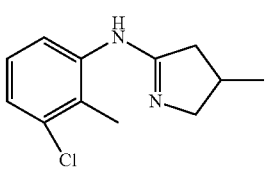
1

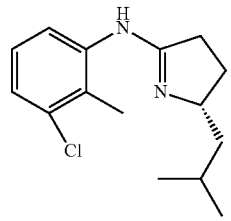
2

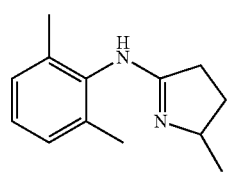
3

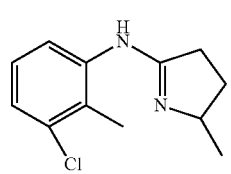
4

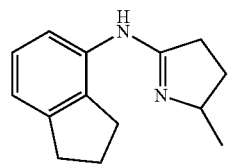
5

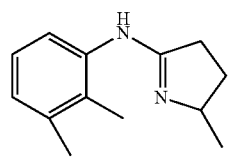
6

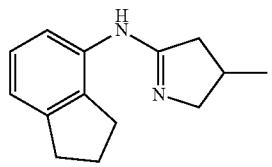
7

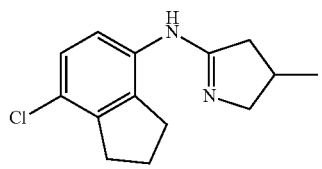
8

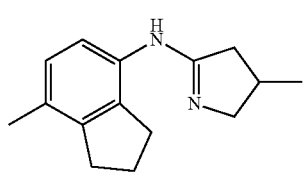
9

Preferably the compounds are chosen from the group consisting of:

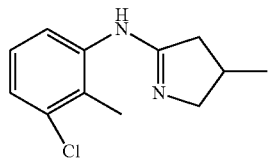
1

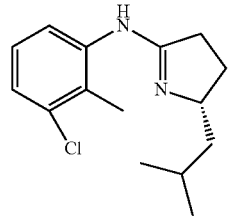
2

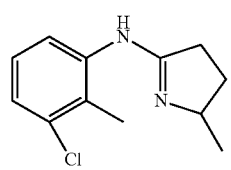
4

-continued

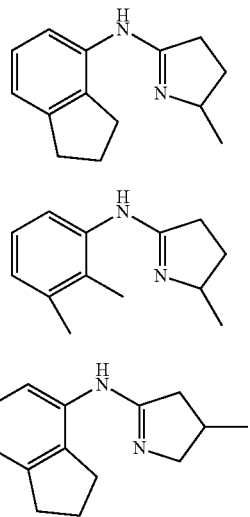

In another advantageous embodiment, the present invention concerns compounds such as defined above, of following general formula (Ic):

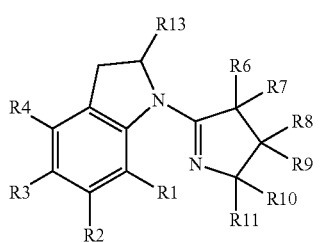

where R1 to R4 and R6 to R11 are such as defined above and R13 represents H or CH₃.

In one particular embodiment of the compounds of general formula (Ic), R13 represents a methyl.

In one particular embodiment of the compounds of general formula (Ic), R1 is not a hydrogen.

In one preferred embodiment of the compounds of general formula (Ic), R13 is a methyl and/or R1 is not a hydrogen. Therefore when R13 is a hydrogen then R1 is not a hydrogen. Similarly, at least one among R1 and R13 is not a hydrogen.

R1 is chosen from the group consisting of a hydrogen, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, CO₂H, CO₂R' where R' is a straight-chain or branched C1-C8 alkyl, and a C3-C6 cycloalkyl, preferably from the group consisting of a hydrogen, a halogen, straight-chain or branched C1 to C8 alkyl, C2-C8 alkene, straight-chain or branched C1 to C8 alkoxy, a polyether chain, C1-C5 perfluoroalkyl, C1-C8 acyl, OH, SH, a primary, secondary or tertiary amine, CN, CO₂H and CO₂R' where R' is a straight-chain or branched C1-C8 alkyl, further preferably from the group consisting of a hydrogen, a halogen, straight-chain or branched C1 to C3 alkyl, straight-chain or branched C1 to C3 alkoxy, C1-C3 perfluoroalkyl and C1-C3 acyl. In one preferred embodiment, R1 is a hydrogen or straight-chain or branched C1 to C3 alkyl, preferably a methyl. Preferably R2, R3 and R4 are hydrogens.

In one particular embodiment of the compounds of general formula (Ic), among R1, R2, R3 and R4 three thereof are hydrogens and the last is chosen from the group consisting of H, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, CO₂H, CO₂R' where R' is a straight-chain or branched C1-C8 alkyl, and a C3-C6 cycloalkyl, preferably from the group consisting of H, a halogen, straight-chain or branched C1 to C8 alkyl, C2-C8 alkene, straight-chain or branched C1 to C8 alkoxy, a polyether chain, C1-C5 perfluoroalkyl, C1-C8 acyl, OH, SH, a primary, secondary or tertiary amine, CN, CO₂H and CO₂R' where R' is a straight-chain or branched C1-C8 alkyl, further preferably from the group consisting of H, a halogen, straight-chain or branched C1 to C3 alkyl, straight-chain or branched C1 to C3 alkoxy, C1-C3 perfluoroalkyl and C1-C3 acyl. In one preferred embodiment, among R1, R2, R3 and R4 three thereof are hydrogens, and the last is a hydrogen or straight-chain or branched C1 to C3 alkyl, preferably a hydrogen or methyl. Preferably, R2, R3 and R4 are hydrogens.

In one particular embodiment of the compounds of general formula (Ic), R6, R7, R9 and R11 are hydrogens, and R8 and R10 are independently chosen from the group consisting of H, a straight-chain or branched C1 to C8 alkyl, C2-C8 alkene, C3-C6 cycloalkyl, C1-C5 perfluoroalkyl, preferably from the group consisting of H and a straight-chain or branched C1 to C8 alkyl, further preferably from the group consisting of H and a straight-chain or branched C1 to C3 alkyl. Preferably, at least one among R8 and R10 is a hydrogen. In one preferred embodiment, R6, R7, R9 and R11 are hydrogens, and R8 and R10 are chosen from the group consisting of H, a straight-chain or branched C to C3 alkyl, preferably from among H and a methyl, at least one of the two being a hydrogen.

The present invention particularly concerns compounds such as defined above of general formula (Ic) wherein:
R1, R2, R3 and R4 are chosen from the group consisting of a hydrogen, a halogen, straight-chain or branched C1 to C3 alkyl, straight-chain or branched C1 to C3 alkoxy, C1-C3 perfluoroalkyl, C1-C3 acyl, OH, SH, a primary, secondary or tertiary amine, —CN, —CO₂H and CO₂R' where R' is a straight-chain or branched C1-C3 alkyl;
R8 and R10 are chosen from the group consisting of a hydrogen and a straight-chain or branched C1 to C5 alkyl, at least one of the two being a hydrogen,
provided that at least one among R1 and R13 is not a hydrogen.

In one particular embodiment of the compounds of general formula (Ic):
R2, R3, R4, R6, R7, R9, R10 and R11 are hydrogens;
R13 is H and R1 is a halogen and straight-chain or branched C1 to C3 alkyl; or R13 is a methyl and R1 is chosen from the group consisting of a hydrogen, a halogen and straight-chain or branched C1 to C3 alkyl; and
R8 and R10 are chosen from the group consisting of a hydrogen and straight-chain or branched C1 to C5 alkyl, at least one of the two being a hydrogen.

In one more particular embodiment of the compounds of general formula (Ic):
R2, R3, R4, R6, R7, R9, R10 and R11 are hydrogens;
R13 is H and R1 is a methyl; or
R13 is a methyl and R1 is chosen from the group consisting of a hydrogen and a methyl; and R8 and R10 are chosen from the group consisting of a hydrogen and a methyl, at least one of the two being a hydrogen.

In another advantageous embodiment, the present invention concerns compounds such as defined above, of following formula (Ic-1):

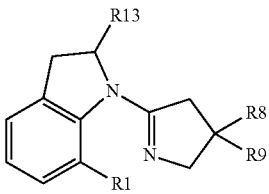

(Ic-1)

where R1, R8 and R9 are such as defined above and R13 represents H or CH$_3$.

Preferably R9 is a hydrogen and at least one group from among R1, R8 and R13 is not a hydrogen. In one embodiment, two groups from among R1, R8 and R13 are not hydrogens.

Preferably, R1 is chosen from the group consisting of H, a halogen, straight-chain or branched C1 to C8 alkyl, C2-C8 alkene, straight-chain or branched C1 to C8 alkoxy, a polyether chain, C1-C5 perfluoroalkyl, C1-C8 acyl, OH, SH, a primary, secondary or tertiary amine, CN, CO$_2$H and CO$_2$R' where R' is a straight-chain or branched C1-C8 alkyl, further preferably from among the group consisting of H, a halogen, straight-chain or branched C1 to C3 alkyl, straight-chain or branched C1 to C3 alkoxy, C1-C3 perfluoroalkyl, C1-C3 acyl. In particular R1 is chosen from the group consisting of H, a halogen, straight-chain or branched C1-C3 alkyl. In particular R1 is H or a methyl.

Preferably R8 is chosen from the group consisting of H, straight-chain or branched C1 to C8 alkyl, more preferably from the group consisting of H and straight-chain or branched C1 to C3 alkyl. In particular R8 is H or a methyl.

In one particular embodiment of the compounds of general formula (IC-1):

R9 is a hydrogen;

R13 is H and R1 is a halogen and C1 to 3 straight-chain or branched alkyl; or

R13 is a methyl and R1 is chosen from the group consisting of a hydrogen, a halogen and straight-chain or branched C1 to C3 alkyl; and R8 and R10 are chosen from the group consisting of a hydrogen and C1-C5 straight-chain or branched alkyl, at least one of the two being a hydrogen.

In a further particular embodiment of the compounds of general formula (Ic-1):

R9 is a hydrogen;

R13 is H and R1 is a methyl; or

R13 is a methyl and R1 is chosen from the group consisting of a hydrogen and a methyl; and R8 and R10 are chosen from the group consisting of a hydrogen and a methyl, at least one of the two being a hydrogen.

In another advantageous embodiment, the present invention concerns compounds such as defined above chosen from among one of the following formulas:

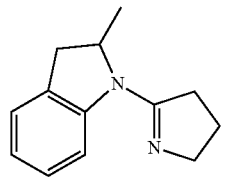

10

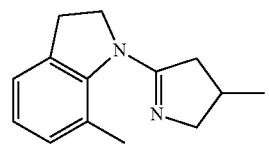

11

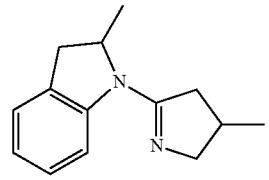

12

The compounds of the invention can be synthesized using methods described in the literature and known to persons skilled in the art, starting from compounds that are commercially available or prepared using techniques known to skilled persons.

According to another aspect, the present invention concerns compounds such as defined above for use thereof in the prevention and/or treatment of metabolic syndrome.

The compounds of the invention, selective for imidazoline receptor IR$_1$ not only allow compounds to be provided that are devoid of side effects related in particular to interaction with the α2-adernergic receptor such as sedation, and maintain a hypotensive effect but which can also be used in monotherapy to treat all the components of metabolic syndrome namely high blood pressure, hypercholesterolaemia, insulin resistance, glucose intolerance and abdominal obesity, thereby avoiding the use of an association of 3 to 6 drugs generating multiple side effects and extra cost for health insurance systems.

Monotherapy and the absence of side effects such as sedation observed in animals should allow the use of the compounds of the invention in the prevention of metabolic syndrome, or of one or more components of metabolic syndrome, in patients at risk for one or other of the said components.

According to another aspect, the present invention concerns a pharmaceutical composition comprising as active ingredient at least one compound defined above, in association with a pharmaceutically acceptable vehicle.

By pharmaceutically acceptable vehicle is to be understood any substance other than the active ingredient in a medicinal product. The addition thereof is intended to impart physicochemical and/or biochemical characteristics to promote administration via oral, sublingual, respiratory, rectal, nasal, intestinal, parenteral route, via intravenous, intraperitoneal, intramuscular, subcutaneous injection, or other characteristics of particular consistency or taste to the end product, preferably avoiding covalent chemical interactions with the active ingredients.

The pharmaceutical compositions of the invention can be in the form of plain or sugar-coated pills, sublingual tablets, soft capsules, hard capsules, tablets, preparations for injection, sprays, nasal drops, suppositories, creams, ointment or dermal gels.

According to another aspect, the present invention concerns a method for treating metabolic syndrome by administering to a patient, in particular via oral route, a pharmaceutical composition containing as active ingredient at least one compound defined above, in association with a pharmaceutically acceptable vehicle, at an effective dose.

In one advantageous embodiment, the present invention concerns a pharmaceutical composition such as defined above that can be administered via oral route.

In one advantageous embodiment, the active ingredient of the pharmaceutical composition that can be administered via oral route as defined above is given at a dose of between 1 mg/kg to 100 mg/kg in man.

Below 1 mg/kg the dose is too small to obtain activity in the treatment of metabolic syndrome, beyond 100 mg/kg there is a risk of the onset of side effects.

The following examples A and 1 to 5 and FIGS. 1 to 8 illustrate the invention.

Chemical Part

Abbreviations Used:

CDCl$_3$: deuterated chloroform iPrOH: Isopropanol

Et$_2$O: Diethyl ether

POCl$_3$: Phosphorus trichloride

TEA: Triethylamine

TMG: Tetramethylguanidine

All the solvents were purified following standard procedures before use. Thin layer chromatography was performed on 60F254 silica plates (Merck) and spots were visualized using a UV lamp. Flash chromatography was performed on S160 silica gel (40-63 µm) as stationary phase. The melting points (m.p.) were determined in open capillaries using Gallenkamp apparatus and not corrected. NMR spectra were recorded in CDCl$_3$ or D$_2$O on a Brucker AV300 spectrometer. Chemical shifts (δ) are expressed in parts per million (ppm), coupling constants are expressed in Hertz (Hz). The abbreviations used for multiplicities are the following: m: non-specified multiplet; s:

singlet; d: doublet; t: triplet; q: quadruplet; qn: quintuplet; hex: hexuplet; h: heptuplet.

Elementary analyses were carried out at the microanalysis department of Université Louis Pasteur, Strasbourg, France. Analytical results obtained for C, H and N are given with ±0.4% of calculated theoretical values. All the target compounds were tested in hydrochloride form. The hydrochlorides were prepared by adding a base ethanol solution (1 eq). The hydrochlorides were recrystallized in iPrOH-Et$_2$O.

EXAMPLE A

General Procedure for Preparing the Aminopyrrolines 1-27 of the Invention

The compounds were synthesized by reaction of the suitable lactame with the corresponding aniline in the presence of POCl$_3$:

Compounds I-27

A.1: General Procedure for Synthesizing the Lactames L (28-33):

A.1.1: Preparation of the Nitroesters 35-38: General Procedure

The α,β-unsaturated ester (39-41) (1 eq) was added in excess (5 eq) to the nitroalkane in an argon atmosphere. A catalytic quantity of tetramethylguanidine (0.1 eq) was added to the mixture which was left under agitation for 12 h at ambient temperature. The excess nitroalkane was distilled under reduced pressure and the residue treated with 2N HCl.

The mixture was extracted with Et$_2$O. The organic phase was washed with water then in brine and finally dried over anhydrous Na$_2$SO$_4$ before the solvent evaporated. The product was distilled under reduced pressure to yield a pure nitroester.

Methyl-4-nitro-butyrate (34) commercial product

Methyl 3-Methyl-4-nitro butyrate (35). Yield 85%, colourless oil, bp 69-70° C. (3 mmHg); $^1$H NMR (CDCl$_3$) δ 4.47 (dd, 1H, ½-CH$_2$, J=6.3, J=12.6); 4.34 (dd, 1H, ½-CH$_2$, J=6.3, J=12.6); 3.69 (s, 3H, CH$_3$); 2.78 (qd, 1H, CH, J=6.8, J=13.5); 2.46 (dd, 1H, ½-CH$_2$, J=6.7, J=16.2); 2.35 (dd, 1H, ½-CH$_2$, J=6.8, J=16.2); 1.09 (d, 3H, CH$_3$, J=6.8).

Methyl 4-Methyl-4-nitro-pentanoate (36). Yield 55%, colourless oil, bp 71-72° C. (2.5 mmHg); $^1$H NMR (CDCl$_3$) δ 3.68 (s, 3H, OCH$_3$); 2.37-2.23 (m, 4H, 2×CH$_2$); 1.59 (s, 6H, 2×CH$_3$).

Methyl 3,3-Dimethyl-4-nitro-butyrate (37). Yield 48%, colourless oil, bp 70-71° C. (1.5 mmHg); $^1$H NMR (CDCl$_3$)

δ 4.52 (s, 2H, CH$_2$); 3.67 (s, 3H, CH$_3$); 2.45 (s, 2H, CH$_2$); 1.15 (s, 6H, 2×CH$_3$).

Methyl 4-(2-methyl-propyl)-4-nitro-pentanoate (38). Yield 45%, oil $^1$H NMR (CDCl$_3$) δ 3.75 (m, 1H); 3.69 (s, 3H); 2.39-2.24 (m, 4H); 1.85 (m, 2H); 1.60 (m, 1H); 0.95 (d, J=7 Hz, 6H).

A.1.2. Preparation of the Lactames L 30-33:

The nitroester 34-38 (100 mmol) was dissolved in 250 ml glacial acetic acid and 500 mg of 10% Pd—C were added. The mixture was hydrogenated at ambient temperature and atmospheric pressure for 12 h. The mixture was filtered and the solvent evaporated. The product was then dissolved in 100 ml of absolute ethanol and alkalinized with triethylamine (TEA). The mixture was heated under reflux for 12 h. The solvents were evaporated under reduced pressure; the residue was diluted in Et$_2$O and 1N HCl was added. The aqueous phase was extracted twice with Et$_2$O. The organic phases were dried over Na$_2$SO$_4$ and the solvent was evaporated. The product was purified by distillation under reduced pressure which led to obtaining of the lactames 30-33.

Pyrrolidin-2-one (28) commercial product

3-Methyl-pyrrolidin-2-one (29) commercial product

4-Methyl-pyrrolidin-2-one (30). Yield 83%, colourless oil (subsequently crystallized), bp 103° C. (6 mmHg); $^1$H NMR (CDCl$_3$) δ 6.75 (br s, 1H, NH); 3.46 (dd, 1H, ½-CH$_2$, J=7.6, J=9.3); 2.93 (dd, 1H, ½-CH$_2$, J=6.0, J=9.5); 2.53-2.44 (m, 1H, CH); 2.46 (dd, 1H, ½-CH$_2$, J=6.9, J=16.3); 1.94 (dd, 1H, ½-CH$_2$, J=7.0, J=16.2); 1.10 (d, 3H, CH$_3$, J=6.9).

5,5-Dimethyl-pyrrolidin-2-one (31). Yield 61%, colourless oil (subsequently crystallized), bp 85-88° C. (2 mmHg); $^1$H NMR (CDCl$_3$) δ 6.52 (br s, 1H, NH): 2.42 (t, 2H, CH$_2$, J=8.0); 1.92 (t, 2H, CH$_2$, J=8.0); 1.28 (s, 6H, 2×CH$_3$).

4,4-Dimethyl-pyrrolidin-2-on (32). Yield 73%, colourless oil (subsequently crystallized), bp 94-95° C. (2 mmHg); $^1$H NMR (CDCl$_3$) δ 6.68 (br s, 1H, NH); 3.06 (s, 2H, CH$_2$); 2.11 (s, 2H, CH$_2$); 1.16 (s, 6H, 2×CH$_3$).

5-(2-methyl-propyl)-pyrrolidin-2-one (33). Yield 67%, viscous oil.

$^1$H NMR (CDCl$_3$) δ 6.68 (m, 1 H); 3.75-3.70 (m, 1 H); 2.38-2.19 (m, 3 H); 1.72-1.60 (m, 2 H); 1.68 (m, 1 H), 1.52-1.42 (m, 1 H); 1.36-1.26 (m, 1 H) 0.93 (d, J=8 Hz, 6 H).

A.1.3 Preparation of Indane Derivatives 42-44

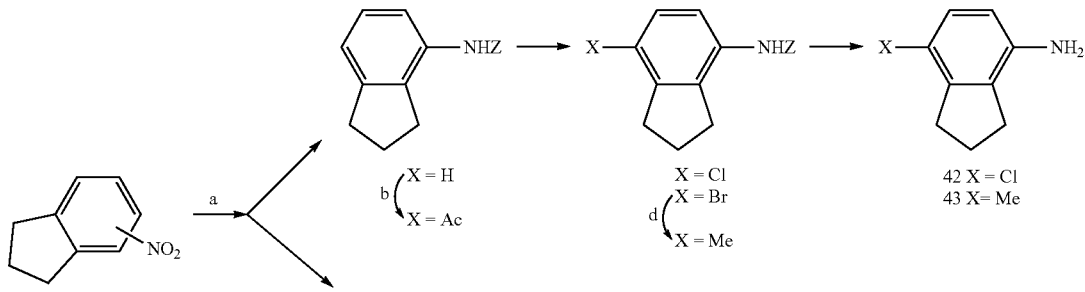

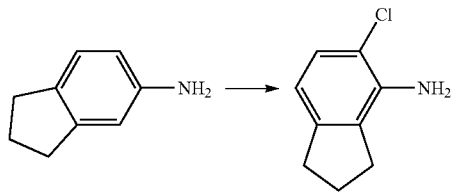

44 a) Indan-4-ylamine and indan-5-ylamine

Nitroindane (commercial mixture of isomers 4 and 5) was subjected to hydrogenation in methanol with 10% Pd/C at ambient temperature for 12 h. The two isomers of indanylamine were separated by flash chromatography (AcOEt-hexane, 3-7) to give indan-4-ylamine (brown oil which crystallizes) with 53% yield, and indan-5-ylamine (brown oil which crystallizes) with 40% yield.

$^1$H NMR (CDCl$_3$) (Inand-4-ylamine) δ 7.69 (d, 1H, Har, J=8.1); 7.18 (t, 1H, Har, J=8.1); 7.04 (d, 1H, Har, J=8.0); 6.88 (br s, 2H, NH$_2$); 2.93 (t, 2H, CH$_2$, J=7.5); 2.84 (t, 2H, CH$_2$, J=7.4); 2.11 (qn, 2H, CH$_2$, J=7.5).

b) Preparation of Indane Derivative 42

The indan-4-ylamine was dissolved in pure acetic anhydride at 0° C. The resulting precipitate which rapidly occurs was filtered and washed with water. The product was collected with a yield of 90% (grey white solid) and was sufficiently pure for use at the following step without further purification.

$^1$H NMR (CDCl$_3$) δ 7.73 (d, 1H, Har, J=8.1); 7.15 (t, 1H, Har, J=8.1); 7.02 (d, 1H, Har, J=8.0); 6.96 (br s, 1H, NH); 2.95 (t, 2H, CH$_2$, J=7.5); 2.81 (t, 2H, CH$_2$, J=7.4); 2.18 (s, 3H, CH$_3$); 2.10 (qn, 2H, CH$_2$, J=7.5).

The above-obtained product (1 g) was dissolved in 20 ml glacial acetic acid and a solution of chlorine in freshly prepared glacial acetic acid was added (1 eq). After 20 min, 30 ml of water were added and the mixture left under agitation for 10 min. The precipitate which occurred was filtered and washed with a saturated aqueous solution of sodium carbonate, with Na$_2$S$_2$O$_5$ and with water. The product was dried in a desiccator which led to the compound 7-chloro-4-acetamidoindane with a yield of 96% in the form of a white solid.

$^1$H NMR (CDCl$_3$) δ 7.72 (d, 1H, Har, J=8.6); 7.12 (d, 1H, Har, J=8.6); 7.0 (br s, 1H NH); 2.99 (t, 2H, CH$_2$, J=7.5); 2.87 (t, 2H, CH$_2$, J=7.5); 2.16 (s, 3H, CH$_3$); 2.11 (qn, 2H, CH$_2$, J=7.5).

The 7-chloro-4-acetamidoindane (1 g) was re-suspended in 50 ml of 4N HCl and the mixture was heated under reflux for 2 h. After cooling, the mixture was washed with AcOEt, alkalinized with NaOH pellets until the pH was slightly basic. The mixture was extracted with Et2O. The organic phase was washed with water, brine and dried over anhydrous sodium sulfate. The solvent was evaporated and the aniline 42 was obtained with near-quantitative yield.

$^1$H NMR (CDCl$_3$) δ 7.01 (d, 1H, Har, J=8.4); 6.47 (d, 1H, Har, J=8.4); 3.55 (br s, 2H, NH$_2$); 2.94 (t, 2H, CH$_2$, J=7.5); 2.83 (t, 2H, CH$_2$, J=7.5); 2.13 (qn, 2H, CH$_2$, J=7.4).

c) Preparation of Indane Derivative 43

The operating mode was the same as for aniline 42 except that bromine was used instead of chlorine.

The compound 7-bromo-4-acetamidoindane was obtained with a yield of 92% in the form of a white solid.

$^1$H NMR (CDCl$_3$) δ 7.65 (d, 1H, Har, J=8.6); 7.28 (d, 1H, Har, J=8.6); 6.89 (br s, 1H, NH); 2.97 (t, 2H, CH$_2$, J=7.6); 2.90 (t, 2H, CH$_2$, J=7.5); 2.18 (s, 3H, CH$_3$); 2.13 (qn, 2H, CH$_2$, J=7.6).

The compound 7-bromo-4-acetamidoindane was dissolved in dioxane (10 ml) and the mixture was degassed and placed in an argon atmosphere. Pd(PPh$_3$)$_4$ (10 mole %) and 5 ml of 2 N Na$_2$CO$_3$ were added. Trimethylboroxine (1.5 eq) was then added to the mixture using a syringe and the whole was heated under reflux for 10 h. After cooling, the reaction mixture was diluted with 5 ml of water and filtered. The mixture was extracted with dichloromethane, the organic phase was dried over anhydrous sodium sulfate and the solvent was evaporated under reduced pressure. The product was purified by flash chromatography (AcOEt-hexane; 3-7) which led to the compound 7-methyl-4-acetamidoindane with a yield of 80% in the form of a white solid.

$^1$H NMR (CDCl$_3$) δ 7.57 (d, 1H, Har, J=8.2); 6.96 (d, 1H, Har, J=8); 6.89 (br s, 1H, NH); 2.86 (t, 2H, CH$_2$, J=7.4); 2.82 (t, 2H, CH$_2$, J=7.4); 2.22 (s, 3H, CH$_3$(ar)); 2.17 (s, 3H, CH$_3$); 2.10 (qn, 2H, CH$_2$, J=7.5).

The 7-methyl-4-acetamidoindane was hydrolyzed in the same manner as for 7-chloro-4-acetamidoindane above. Compound 43 was obtained in the form of brown oil with a yield of 95%.

$^1$H NMR (CDCl$_3$) δ 6.81 (d, 1H, Har, J=7.7); 6.46 (d, 1H, Har, J=7.8); 3.44 (br s, 2H, NH$_2$); 2.84 (t, 2H, CH$_2$, J=7.5); 2.76 (t, 2H, CH$_2$, J=7.4); 2.18 (s, 3H, CH$_3$(ar)); 2.12 (qn, 2H, CH$_2$, J=7.5).

d) Preparation of Derivative 44

The protocol used was the same as for derivative 42 but the starting product was indan-5-ylamine.

$^1$H NMR (CDCl$_3$) δ 7.11 (s, 1H, Har); 6.72 (s, 1H, Har); 3.92 (br s, 2H, NH$_2$); 2.81 (t, 4H, 2×CH$_2$, J=7.5); 2.03 (qn, 2H, CH$_2$, J=7.4).

A.1.4 Preparation of Aminopyrrolines 1-27

A solution of suitable lactame 28-33 (5 mmol) and of the chosen aniline derivative was prepared in dichloroethane (10 ml) in an argon atmosphere. POCl$_3$ (1 eq) was added dropwise to the mixture which was then heated to 60° C. for 6 h. The mixture was cooled and hydrolyzed with 5 ml of a saturated aqueous solution of Na$_2$CO$_3$. The aqueous phase was extracted twice with dichloromethane. The organic phase was dried over anhydrous sodium sulfate and the solvent was evaporated under reduced pressure.

The product was purified by flash chromatography (3% TEA in AcOEt) leading to one of the aminopyrrolines 1-27.

The products obtained are characterized below via their NMR spectrum.

(3-Chloro-2-methyl-phenyl)-(4-methyl-4,5-dihydro-3H-pyrrol-2-yl)-amine hydrochloride (1)

$^1$H NMR (D$_2$O) δ 7.45 (d, 1H, Har, J=7.9); 7.25 (d, 1H, Har, J=7.9); 7.20 (t, 1H, Har, J=7.8); 3.73-3.68 (m, 1H, ½CH$_2$); 3.22-3.16 (m, 2H, ½CH$_2$+CH); 2.77-2.71 (m, 2H, CH$_2$); 2.22 (s, 3H, CH$_3$); 1.10 (d, 3H, CH$_3$, J=6.5). $^{13}$C NMR (D$_2$O) δ 169.1; 135.5; 133.4; 132.3; 130.1; 128.1; 125.3; 54.2; 37.9; 29.5; 18.1; 14.2. Anal. (C$_{12}$H$_{15}$ClN$_2$, HCl) C, H, N.

(3-Chloro-2-methyl-phenyl)-(5-(2-methyl-propyl)-4,5-dihydro-3H-pyrrol-2-yl)-amine hydrochloride (2)

$^1$H-NMR (400 MHz, MeOH-d4) δ 7.54 (d, 1H, J=8 Hz), 7.36 (m, 2H), 4.12 (m, 1H), 3.18 (m, 2H), 2.36 (s, 3H), 1.95 (s, 1H), 1.66 (m, 2H), 1.46 (m, 1H), 0.95 (d, 6H, J=8 Hz).

$^{13}$C NMR δ (100 MHz, MeOH-d4) δ 131.2, 129.4, 126.5, 61.6, 61.4, 31.5, 31.4, 27.9, 27.8, 26.2, 23.6, 23.5, 22.6, 22.4, 15.2.

ESI-MS (m/z): [M+H]$^+$ calculated for C$_{15}$H$_{22}$ClN$_2$: 265. Found: 265.

(2,6-Dimethyl-phenyl)-(5-methyl-4,5-dihydro-3H-pyrrol-2-yl)-amine hydrochloride (3)

$^1$H NMR (D2O) δ 7.24 (d, 1H, Har, J=7.6); 7.17 (t, 1H, Har, J=7.7); 7.06 (d, 1H, Har, J=7.6); 4.02 (h, 1H, CH, J=6.4); 3.09-2.97 (m, 2H, CH$_2$); 2.37-2.31 (m, 1H, ½CH$_2$); 2.24 (s, 3H, CH$_3$); 2.08 (s, 3H, CH$_3$); 1.86-1.75 (m, 1H, ½CH$_2$); 1.13 (d, 3H, CH$_3$, J=6.4). $^{13}$C NMR (D$_2$O) δ 168.2; 139.2; 133.5; 133.1; 131.2; 126.6; 124.0; 56.2; 43.8; 37.0; 28.6; 24.9; 17.2. Anal. (C$_{13}$H$_{18}$N$_2$.HCl) C, H, N.

(3-Chloro-2-methyl-phenyl)-(5-methyl-4,5-dihydro-3H-pyrrol-2-yl)-amine hydrochloride (4)

$^1$H NMR (CDCl$_3$) δ 7.41 (d, 1H, Har, J=7.8); 7.23 (d, 1H, Har, J=7.9); 7.18 (t, 1H, Har, J=7.8); 4.02 (h, 1H, CH, J=6.4); 3.11-3.05 (m, 2H, CH$_2$); 2.38-2.30 (m, 1H, ½CH$_2$); 2.25 (s, 3H, CH$_3$); 2.11 (s, 3H, CH$_3$); 1.88-1.78 (m, 1H, ½CH$_2$); 1.13 (d, 3H, CH$_3$, J=6.4). $^{13}$C NMR (D$_2$O) δ 168.7; 139.5; 133.4; 132.8; 130.5; 126.8; 123.7; 56.2; 32.3; 30.5; 29.7; 24.9; 20.2. Anal. (C$_{12}$H$_{15}$ClN$_2$, HCl) C, H, N.

Indan-4-yl-(5-methyl-4,5-dihydro-3H-pyrrol-2-yl)-amine hydrochloride (5)

$^1$H NMR (D$_2$O) δ 7.28 (d, 1H, Har, J=7.5); 7.21 (t, 1H, Har, J=7.6); 7.02 (d, 1H, Har, J=7.6); 4.07 (h, 1H, CH, J=6.4); 3.04-2.88 (m, 2H, CH$_2$); 2.88 (t, 2H, CH$_2$, J=7.5); 2.74 (t, 2H, CH$_2$, J=7.4); 2.37 (m, 1H, ½CH$_2$); 2.00 (qn, 2H, CH$_2$, J=7.3); 1.83-1.75 (m, 1H, ½CH$_2$); 1.17 (d, 3H, CH$_3$, J=6.4). $^{13}$C NMR (D$_2$O) δ 168.0; 147.6; 140.3; 130.7; 127.9; 125.0; 122.6; 56.8; 32.6; 30.1; 29.9; 28.2; 24.8; 19.9. Anal. (Cl$_4$H is N$_2$, HCl) C, H, N.

(2,3-Dimethyl-phenyl)-(5-methyl-4,5-dihydro-3H-pyrrol-2-yl)-amine hydrochloride (6)

$^1$H NMR (D$_2$O) δ 7.24 (d, 1H, Har, J=7.6); 7.17 (t, 1H, Har, J=7.7); 7.06 (d, 1H, Har, J=7.6); 4.02 (h, 1H, CH, J=6.4); 3.09-3.01 (m, 2H, CH$_2$); 2.39-2.29 (m, 1H, ½CH$_2$); 2.24 (s, 3H, CH$_3$); 2.08 (s, 3H, CH$_3$); 1.85-1.78 (m, 1H, ½CH$_2$); 1.13 (d, 3H, CH$_3$, J=6.4). $^{13}$C NMR (D$_2$O) δ 168.2; 139.2; 133.5; 133.1; 131.2; 126.6; 124.0; 56.2; 43.8; 37.0; 28.6; 24.9; 17.2. Anal. (C$_{13}$H$_{18}$N$_2$, HCl) C, H, N.

Indan-4-yl-(4-methyl-4,5-dihydro-3H-pyrrol-2-yl)-amine hydrochloride (7)

$^1$H NMR (D$_2$O) δ 7.28 (d, 1H, Har, J=7.5); 7.21 (t, 1H, Har, J=7.6); 7.03 (d, 1H, Har, J=7.5); 3.70 (dd, 1H, ½CH$_2$, J=10.8, J=7.8); 3.19 (dd, 1H, ½CH$_2$, J=11, J=6); 3.17-3.11 (m, 1H, ½CH$_2$); 2.89 (t, 2H, CH$_2$, J=7.4); 2.74 (t, 2H, CH$_2$, J=7.4); 2.68-2.61 (m, 2H, CH+½CH$_2$); 2.01 (qn, 2H, CH$_2$, J=7.5); 1.10 (d, 3H, CH$_3$, J=7). $^{13}$C NMR (D$_2$O) δ 168.3; 147.6; 140.2; 130.5; 127.9; 124.9; 122.5; 54.1; 37.8; 32.6; 29.9; 29.5; 24.7; 17.6. Anal. (C$_{14}$H$_{18}$N$_2$, HCl) C, H, N.

(7-Chloro-indan-4-yl)-(4-methyl-4,5-dihydro-3H-pyrrol-2-yl)-amine hydrochloride (8)

$^1$H NMR (D$_2$O) δ 7.22 (d, 1H, Har, J=8.3); 7.01 (d, 1H, Har, J=8.4); 3.70 (dd, 1H, ½CH$_2$, J=10.9, J=7.7); 3.20 (dd, 1H, ½CH$_2$, J=10.9, J=7.2); 3.15-3.09 (m, 1H, ½CH$_2$); 2.93 (t, 2H, CH$_2$, J=7.6); 2.82 (t, 2H, CH$_2$, J=7.5); 2.69-2.61 (m, 2H, CH+½CH$_2$); 2.04 (qn, 2H, CH$_2$, J=7.6); 1.08 (d, 3H, CH$_3$, J=6.8). $^{13}$C NMR (D$_2$O) δ 168.5; 145.2; 142.4; 130.4; 129.1; 127.8; 124.5; 54.2; 37.9; 32.2; 30.9; 29.5; 23.8; 17.7. Anal. (C$_{14}$H$_{17}$ClN$_2$, HCl) C, H, N.

(7-Methyl-indan-4-yl)-(4-methyl-4,5-dihydro-3H-pyrrol-2-yl)-amine hydrochloride (9)

$^1$H NMR (D$_2$O) δ 7.06 (d, 1H, Har, J=8); 6.95 (d, 1H, Har, J=8); 3.7 (dd, 1H, ½CH$_2$, J=10.8, J=7.7); 3.21-3.09 (m, 2H, ½CH$_2$+CH); 2.82 (t, 2H, CH$_2$, J=7.5); 2.75 (t, 2H, CH$_2$, J=7.5); 2.70-2.64 (m, 2H, CH$_2$); 2.19 (s, 3H, CH$_3$); 2.01 (qn, 2H, CH$_2$, J=7.5); 1.09 (d, 3H, CH$_3$, J=6.7). $^{13}$C NMR (D$_2$O) δ 168.4; 145.9; 139.8; 135.2; 132.4; 128.5; 128.1; 122.8; 54.0; 37.8; 31.3; 30.1; 29.6; 24.2; 18.1; 17.7. Anal. (C$_{15}$H$_{20}$N$_2$, HCl) C, H, N.

1-(3,4-dihydro-2H-pyrrol-5-yl)-2-methylindoline hydrochloride (10)

$^1$H NMR (400 MHz, MeOH-d4) δ 7.44-7.29 (m, 4H); 4.74 (m, 1H); 3.86 (m, 2H); 6.62-3.56 (m, 2H); 3.29-3.23 (1H); 2.88-2.84 (m, 1H); 2.41-2.32 (m, 2H); 1.35 (d, 3H, J=5 Hz). C-NMR δ (100 MHz, MeOH-d4 δ 116.7; 140.5; 134.5; 129.3; 128.0; 127.9; 117.0; 61.8; 37.0; 33.1; 22.1; 19.3.
ESI-MS (m/z): [M+H]$^+$ calculated for C$_{13}$H$_{17}$N$_2$: 201. Found: 201.

7-methyl-1-(3-methyl-3,4-dihydro-2H-pyrrol-5-yl)indoline hydrochloride (11)

$^1$H NMR (400 MHz, MeOH-d4) δ 7.28-7.20 (m, 3H); 4.282-4.24 (m, 2H); 3.98-3.93 (m, 1H); 3.46-3.39 (m, 2H); 3.23-3.20 (m, 2H); 2.95-84 (m, 2H); 2.29 (s, 3H); 1.26 (d, 3H, J=8 Hz).
$^{13}$C NMR δ (100 MHz, MeOH-d4) δ 168.4; 140.1; 137.8; 131.9; 129.5; 128.8; 124.3; 57.0; 56.2; 54.9; 41.2; 31.6; 31.0; 19.4; 18.7.
ESI-MS (m/z): [M+H]$^+$ calculated for C$_{13}$H$_{19}$N$_2$: 215. Found: 215.

2-methyl-1-(3-methyl-3,4-dihydro-2H-pyrrol-5-yl)indoline hydrochloride (mixture of diastereoisomers) (12)

Oil, $^1$H NMR (400 MHz, acetone-d6) δ 7.43-7.17 (m, 4H); 5.30-5.28 (m, 1H); 3.96-3.85 (m, 2H); 3.53-3.27 (m, 3H); 2.91-2.74 (m, 3H); 1.32-1.04 (m, 6H).
$^{13}$C NMR δ (100 MHz, acetone-d6) δ 164.9 (164.4); 140.7; 134.2; 128.7; 127.4; 116.7 (116.6); 61.2 (61.1); 40.6 (40.4); 31.7; 30.4); 25.7; 19.9 (19.8); 18.0
ESI-MS (m/z): [M+H]$^+$ calculated for C$_{13}$H$_{19}$N$_2$: 215. Found: 215.

(2-Chlorophenyl)-(5-methyl-4,5-dihydro-3H-pyrrol-2-yl)-amine hydrochloride (13)

mp 173-4° C. $^1$H NMR (D$_2$O) δ 7.67 (m, 1H, Har); 7.50-7.53 (m, 3H, Har); 4.21 (m, 1H, CH); 3.18 (m, 2H, CH$_2$); 2.51 (m, 1H, ½CH$_2$); 1.94 (m, 1H, ½CH$_2$); 1.30 (d, 3H, CH$_3$). $^{13}$C NMR (D$_2$O) δ 168.1; 132.5; 131.4; 131.3; 131.0; 129.3; 128.6; 57.9; 30.9; 28.8; 20.5. Anal. (C$_{11}$H$_{13}$ClN$_2$, HCl) C, H, N.

(2-Fluoro-5-methyl-phenyl)-(5-methyl-4,5-dihydro-3H-pyrrol-2-yl)-amine hydrochloride (14)

$^1$H NMR (D$_2$O) δ 7.20-7.09 (m, 3H, Har); 4.11 (hex, 1H, CH, J=6.8); 3.09-2.98 (m, 2H, CH$_2$); 2.42-2.37 (m, 1H, ½CH$_2$); 2.25 (s, 3H, CH$_3$); 1.85-1.73 (m, 1H, ½CH$_2$); 1.08 (d, 3H, CH$_3$, J=6.5). $^{13}$C NMR (D$_2$O) δ 168.4; 154.3 (d, J$^1_{C-F}$=244.5); 135.7; 130.9; 126.9; 121.6 (d, J$^2_{C-F}$=13.2); 116.4 (d, J$^2_{C-F}$=19.5); 57.2; 30.5; 28.1; 21.3; 19.7. $^{19}$F NMR (D$_2$O) δ −128.3. Anal. (C$_{12}$H$_{15}$FN$_2$, HCl) C, H, N.

(2-Chloro-5-methyl-phenyl)-(5-methyl-4,5-dihydro-3H-pyrrol-2-yl)-amine hydrochloride (15)

$^1$H NMR (D$_2$O) δ 7.38 (dd, 1H, Har, J=3.1., J=7.8); 7.18 (d, 1H, Har, J=2.9); 7.16 (dd, 1H, Har, J=3.0, J=7.7); 4.09-3.96

(m, 1H, CH); 3.07-2.94 (m, 2H, CH$_2$); 2.41-2.33 (m, 1H, ½CH$_2$); 2.24 (s, 3H, CH$_3$); 1.82-1.72 (m, 1H, ½CH$_2$); 1.16 (d, 3H, CH$_3$, J=6.3). $^{13}$C NMR (D$_2$O) δ 168.5; 139.4; 131.2; 130.2; 128.0; 126.8; 124.4; 57.1; 30.2; 28.1; 19.8; 19.7. Anal. (C$_{12}$H$_{15}$ClN$_2$, HCl) C, H, N.

(4-Fluoro-2-methyl-phenyl)-(5-methyl-4,5-dihydro-3H-pyrrol-2-yl)-amine hydrochloride (16)

$^1$H NMR (D$_2$O) δ 7.22 (dd, 1H, Har, J=5.4, J=8.7); 7.09 (dd, 1H, Har, J=2.9, J=8.7); 7.0 (dt, 1H, Har, J=2.9, J=8.8); 4.14 (hex, 1H, CH, J=6.7); 3.11-3.03 (m, 2H, CH$_2$); 2.45-2.97 (m, 1H, ½CH$_2$); 2.17 (s, 3H, CH$_3$); 1.81-1.74 (m, 1H, ½CH$_2$); 1.11 (d, 3H, CH$_3$, J=6.4). $^{13}$C NMR (D$_2$O) δ 169.8; 161.9 (d, J$^1_{C-F}$=248.8); 137.8; (d, J$^3_{C-F}$)=9.2); 129.3 (d, J$^4_{C-F}$=2.8); 128.3 (d, J$^3_{C-F}$=9.6); 117.5 (d, J$^2_{C-F}$=22.7); 114.2 (d, J$^2_{C-F}$=23.0); 55.6; 31.5; 28.8; 19.7; 19.5. $^{19}$F NMR (D$_2$O) δ 113.4. Anal. (C$_{12}$H$_{15}$FN$_2$, HCl) C, H, N.

(5,6,7,8-tetrahydro-naphthalen-1-yl)-(5-Methyl-4,5-dihydro-3H-pyrrol-2-yl)-amine hydrochloride (17)

$^1$H NMR (D$_2$O) δ 7.17 (d, 2H, Har, J=7); 7.03 (t, 1H, Har, J=7.1); 4.06-4.00 (m, 1H, CH); 3.04-2.97 (m, 2H, CH$_2$); 2.72 (t, 2H, CH$_2$, J=5.7); 2.51 (t, 2H, CH$_2$, J=5.9); 2.40-2.32 (m, 1H, ½CH$_2$); 1.81-1.61 (m, 5H, ½CH$_2$+2×CH$_2$); 1.15 (d, 3H, CH$_3$, J=6.4). $^{13}$C NMR (D$_2$O) δ 168.6; 140.1; 133.9; 133.0; 130.2; 126.6; 123.6; 56.6; 29.9; 28.9; 28.2; 24.1; 22.1; 22.0; 19.8. Anal. (C$_{15}$H$_{20}$N$_2$, HCl) C, H, N.

Indan-5-yl-(5-methyl-4,5-dihydro-3H-pyrrol-2-yl)-amine hydrochloride (18)

$^1$H NMR (D$_2$O) δ 7.26 (d, 1H, Har, J=8.0); 7.08 (d, 1H, Har, J=1.5); 6.96 (dd, 1H, Har, J=1.9, J=7.9); 4.03 (h, 1H, CH, J=6.6); 2.99-2.92 (m, 2H, CH$_2$); 2.80 (t, 4H, 2×CH$_2$, J=7.5); 2.35-2.29 (m, 1H, ½CH$_2$); 1.97 (qn, 2H, CH$_2$, J=7.5); 1.79-1.71 (m, 1H, ½CH$_2$); 1.16 (d, 3H, CH$_3$, J=6.4). $^{13}$C NMR (D$_2$O) δ 167.7; 145.7; 145.1; 132.7; 125.5; 121.9; 120.1; 56.9; 32.3; 32.0; 30.4; 28.0; 25.3; 19.8. Anal. (C$_{14}$H$_{18}$N$_2$, HCl) C, H, N.

(6-Chloro-indan-5-yl)-(5-methyl-4,5-dihydro-3H-pyrrol-2-yl)-amine hydrochloride (19)

$^1$H NMR (D$_2$O) δ 7.18 (s, 1H, Har); 6.91 (s, 1H, Har); 4.07 (h, 1H, CH, J=6.6); 2.97-2.90 (m, 2H, CH$_2$); 2.81 (t, 4H, 2×CH$_2$, J=7.5); 2.36-2.28 (m, 1H, ½CH$_2$); 1.97 (qn, 2H, CH$_2$, J=7.5); 1.79-1.71 (m, 1H, ½CH$_2$); 1.63 (d, 3H, CH$_3$, J=6.4). $^{13}$C NMR (D$_2$O) δ 168.5; 145.3; 145.9; 133.4; 127.5; 122.7; 121.6; 57.2; 32.2; 31.8; 30.6; 27.9; 25.5; 21.1. Anal. (C$_{14}$H$_{17}$ClN$_2$, HCl) C, H, N.

(7-Chloro-indan-4-yl)-(5-methyl-4,5-dihydro-3H-pyrrol-2-yl)-amine hydrochloride (2)

$^1$H NMR (D$_2$O) δ 7.22 (d, 1H, Har, J=8.3); 7.01 (d, 1H, Har, J=8.4); 4.05 (h, 1H, CH, J=6.4); 3.05-2.99 (m, 2H, CH$_2$); 2.93 (t, 2H, CH$_2$, J=7.6); 2.81 (t, 2H, CH$_2$, J=7.5); 2.40-2.32 (m, 1H, ½CH$_2$); 2.03 (qn, 2H, CH$_2$, J=7.6); 1.82-1.77 (m, 1H, ½CH$_2$); 1.17 (d, 3H, CH$_3$, J=6.4). $^{13}$C NMR (D$_2$O) δ 168.4; 145.1; 142.5; 130.5; 129.2; 127.8; 124.4; 56.8; 32.6; 30.1; 29.9; 28.2; 24.8; 19.9. Anal. (C$_{14}$H$_1$ClN$_2$, HCl) C, H, N.

(2,3-Dimethyl-phenyl)-(4-methyl-4,5-dihydro-3H-pyrrol-2-yl)-amine hydrochloride (21)

$^1$H NMR (D$_2$O) δ 7.21 (d, 1H, Har, J=7.7); 7.16 (t, 1H, Har, J=7.7); 7.03 (d, 1H, Har, J=7.6); 3.71-3.65 (m, 1H, ½CH$_2$); 3.23-3.17 (m, 2H, ½CH$_2$+CH); 2.74-2.70 (m, 2H, CH$_2$); 2.30 (s, 3H, CH$_3$); 2.11 (s, 3H, CH$_3$); 1.12 (s, 6H, 2×CH$_3$). $^{13}$C NMR (D$_2$O) δ 168.7; 139.5; 133.4; 132.8; 130.5; 126.8; 123.7; 54.5; 43.7; 37.0; 25.6; 19.4; 12.3. Anal. (C$_{13}$H$_{18}$N$_2$, HCl) C, H, N.

Indan-5-yl-(4-methyl-4,5-dihydro-3H-pyrrol-2-yl)-amine hydrochloride (22)

$^1$H NMR (D$_2$O) δ 7.26 (d, 1H, Har, J=8.0); 7.08 (d, 1H, Har, J=1.5); 6.96 (dd, 1H, Har, J=1.9, J=7.9); 4.03 (h, 1H, CH, J=6.6); 2.97-2.93 (m, 2H, CH$_2$); 2.80 (t, 4H, 2×CH$_2$, J=7.5); 2.35-2.29 (m, 1H, ½CH$_2$); 1.97 (qn, 2H, CH$_2$, J=7.5); 1.79-1.71 (m, 1H, ½CH$_2$); 1.16 (d, 3H, CH$_3$, J=6.4). $^{13}$C NMR (D$_2$O) δ 167.7; 145.7; 145.1; 132.7; 125.5; 121.9; 120.1; 56.9; 32.3; 32.0; 30.4; 28.0; 25.3; 19.8. Anal. (C$_{14}$H$_{18}$N$_2$, HCl) C, H, N.

(5,6,7,8-tetrahydro-naphthalen-1-yl)-(4-Methyl-4,5-dihydro-3H-pyrrol-2-yl)-amine hydrochloride (23)

$^1$H NMR (D$_2$O) δ 7.17 (d, 2H, Har, J=7); 7.03 (t, 1H, Har, J=7.1); 4.07-3.99 (m, 1H, CH); 3.04-2.96 (m, 2H, CH$_2$); 2.72 (t, 2H, CH$_2$, J=5.7); 2.51 (t, 2H, CH$_2$, J=5.9); 2.39-2.33 (m, 1H, ½CH$_2$); 1.81-1.61 (m, 5H, ½CH$_2$+2×CH$_2$); 1.15 (d, 3H, CH$_3$, J=6.4). $^{13}$C NMR (D$_2$O) δ 168.6; 140.1; 133.9; 133.0; 130.2; 126.6; 123.6; 56.6; 29.9; 28.9; 28.2; 24.1; 22.1; 22.0; 19.8. Anal. (C$_{15}$H$_{20}$N$_2$, HCl) C, H, N.

Indan-4-yl-(5,5-dimethyl-4,5-dihydro-3H-pyrrol-2-yl)-amine (24) hydrochloride (24)

$^1$H NMR (D$_2$O) δ 7.27 (t, 1H, Har, J=8); 7.19 (d, 1H, Har, J=7.5); 7.01 (d, 1H, Har, J=7.6); 3.08 (t, 2H, CH$_2$, J=7.9); 2.88 (t, 2H, CH$_2$, J=7.5); 2.76 (t, 2H, CH$_2$, J=7.6); 2.13-1.95 (m, 4H, 2×CH$_2$); 1.27 (s, 6H, 2×CH$_3$). $^{13}$C NMR (D$_2$O) δ 166.7; 147.5; 140.3; 130.6; 127.9; 125.0; 122.7; 64.7; 34.3; 32.6; 30.0; 29.7; 26.8; 24.8. Anal. (C$_{15}$H$_{21}$ClN$_2$, HCl) C, H, N.

(3-Chloro-2-methyl-phenyl)-(5,5-dimethyl-4,5-dihydro-3H-pyrrol-2-yl)-amine hydrochloride (25)

$^1$H NMR (D$_2$O) δ 7.40 (d, 1H, Har, J=7.9); 7.21 (d, 1H, Har, J=7.9); 7.18 (t, 1H, Har, J=7.8); 3.08 (t, 2H, CH$_2$, J=7.6); 2.19 (s, 3H, CH$_3$); 1.95 (t, 2H, CH$_2$, J=7.8); 1.26 (s, 6H, 2×CH$_3$). $^{13}$C NMR (D$_2$O) δ 166.7; 135.5; 133.4; 130.1; 128.1; 125.3; 65.0; 37.4; 29.6; 26.8; 24.9. Anal. (C$_{13}$H$_{17}$ClN$_2$, HCl) C, H, N.

(2,3-Dimethyl-phenyl)-(4,4-dimethyl-4,5-dihydro-3H-pyrrol-2-yl)-amine hydrochloride (26)

$^1$H NMR (D$_2$O) δ 7.24 (d, 1H, Har, J=7.6); 7.17 (t, 1H, Har, J=7.7); 7.06 (d, 1H, Har, J=7.6); 3.32 (s, 2H, CH$_2$); 2.87 (s, 2H, CH$_2$); 2.25 (s, 3H, CH$_3$); 2.09 (s, 3H, CH$_3$); 1.16 (s, 6H, 2×CH$_3$). $^{13}$C NMR (D$_2$O) δ 168.7; 139.5; 133.4; 132.8; 130.5; 126.8; 123.7; 59.2; 43.7; 37.0; 25.6; 19.4; 12.3. Anal. (C$_{14}$H$_{20}$N$_2$, HCl) C, H, N.

(3-Chloro-2-methyl-phenyl)-(4,4-dimethyl-4,5-dihydro-3H-pyrrol-2-yl)-amine hydrochloride (27)

$^1$H NMR (D$_2$O) δ 7.45 (d, 1H, Har, J=7.9); 7.25 (d, 1H, Har, J=7.9); 7.20 (t, 1H, Har, J=7.8); 3.70 (m, 1H, ½CH$_2$); 3.19 (m, 2H, ½CH$_2$+CH); 2.74 (m, 2H, CH$_2$); 2.22 (s, 3H, CH$_3$); 1.10 (d, 3H, CH$_3$, J=6.5). $^{13}$C NMR (D$_2$O) δ 169.1;

135.5; 133.4; 130.1; 128.1; 125.3; 54.2; 37.9; 29.5; 18.1; 14.2. Anal. ($C_{13}H_{17}ClN_2$, HCl) C, H, N.

DESCRIPTION OF THE FIGURES

FIG. 1A illustrates competitive binding assays to [$^{125}$I]-PIC in membranes of 3T3 cells and 1B illustrates competitive binding assays to [$^{125}$I]-PIC in membranes of PC12 cells conducted conforming to Example 1.3. Each point is the mean of 2 to 4 experiments conducted in triplet.

FIG. 1A: the Y-axis represents specific binding to [$^{125}$I]PIC and the X-axis represents the log [M] for clonidine (square) and compound 1 according to the invention (triangles).

FIG. 1B: the Y-axis represents specific binding to [$^{125}$I]PIC and the X-axis represents the log [M] of compound 1.

The Y-axis represents the secretion of adiponectin expressed in ng/ml/mg proteins.

The X-axis from left to right represents: black histogram: control group; white histogram: group treated with Efaroxan (100 μmol/ml); grey histogram: group treated with compound 1 (3 μmol/ml); hatched histogram: group treated with compound 1 (3 μmol/ml)+Efaroxan (100 μmol/ml).

FIG. 3 gives the list of systems on which the displacement of specific binding by compound 1 was measured according to Example 3.

Figure 4:
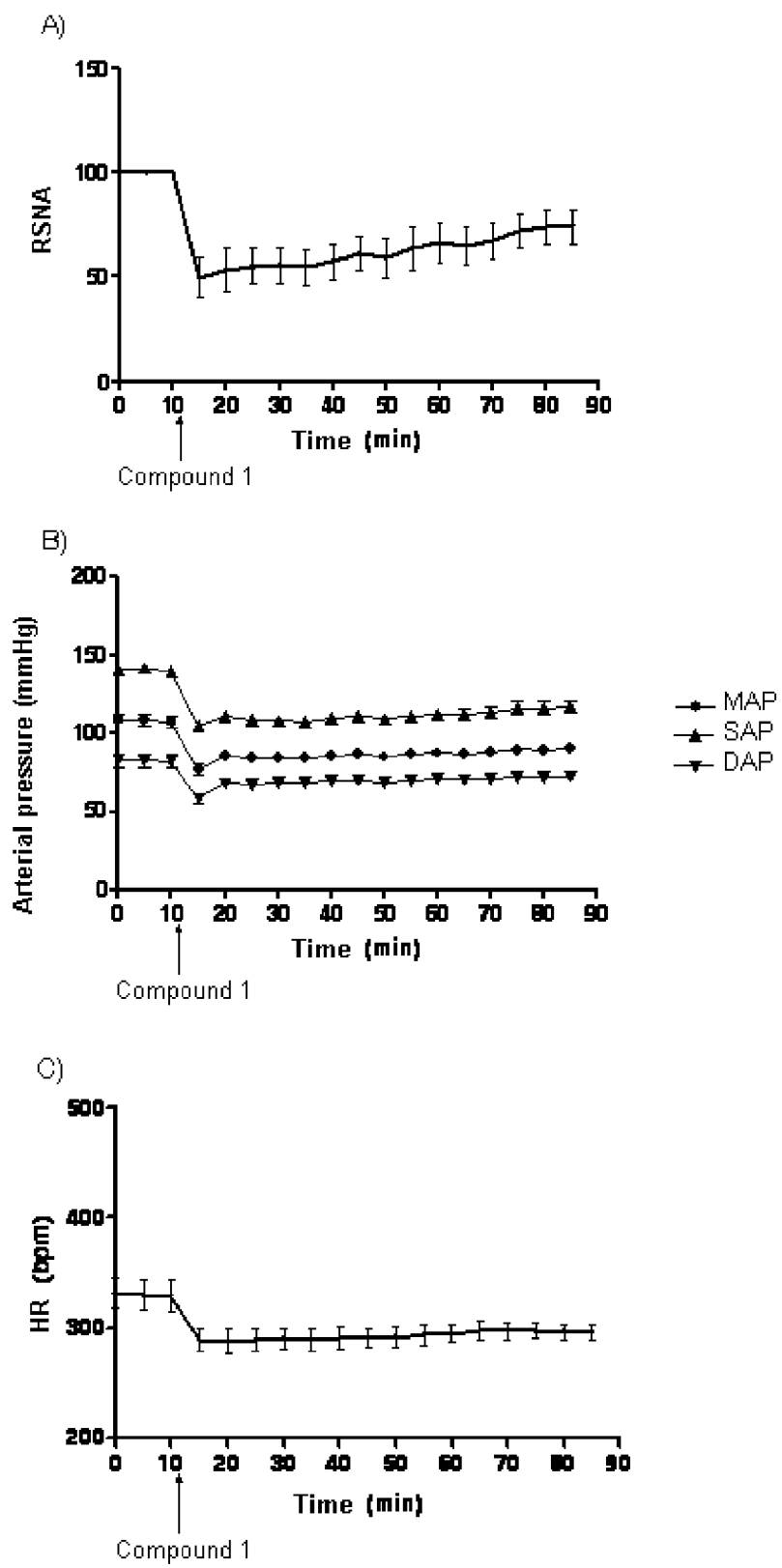

FIGS. 4A to 4C illustrate the effects of acute treatment with compound 1 at a dose of 10 mg/kg (i.v.) on hemodynamic parameters and sympathetic activity in Sprague-Dawley rats anesthetized with urethane (1.5 g/kg i.p.) conforming to Example 4.

FIG. 4A shows the variation in sympathetic renal function as a function of time.

Y-axis: measurement of sympathetic renal activity.

X-axis: time in minutes (the arrow indicates the administration time of compound 1).

FIG. 4B shows the variation in arterial pressure in mm Hg as a function of time. The black circles represent mean arterial pressure; the black diamonds pointing upwards represent systolic arterial pressure and the black diamonds pointing downwards represent diastolic arterial pressure.

Y-axis: measurement of mean (MAP), systolic (SAP) and diastolic (DAP) arterial pressure.

X-axis: time in minutes (the arrow indicates the administration time of compound 1).

FIG. 4C shows the variation in heart rate (HR) in bpm as a function of time.

Y-axis: heart rate (HR) expressed in beats per minute (bpm).

X-axis: time in minutes (the arrow shows the administration time of compound 1).

Figure 5:
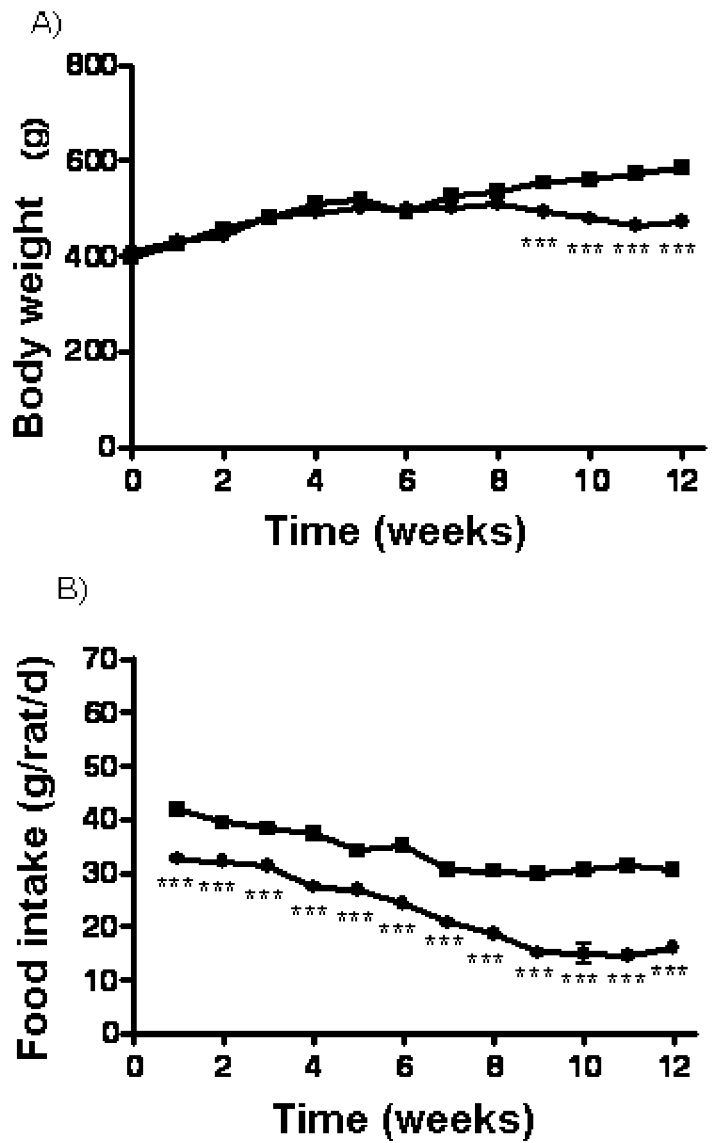

FIGS. 5A and 5B show the effects of chronic treatment with compound 1 (20 mg/kg/d in drinking water) on body weight (FIG. 5A) and food consumption (FIG. 5B) in SHHF rats (spontaneously hypertensive, heart failure) over a 12-week treatment period measured conforming to Example 5.

FIG. 5A: Y-axis: body weight in grams; X-axis: time in weeks.

The black squares represent controls and the black circles represent the group treated with compound 1. ***: $p<0.001$ (ANOVA 2 factors).

FIG. 5B: Y-axis: food consumption in grams/rat/day; X-axis: time in weeks.

The black squares represent controls and the black circles represent the group treated with compound 1. ***: $p<0.001$ (ANOVA 2 factors).

Figure 6:
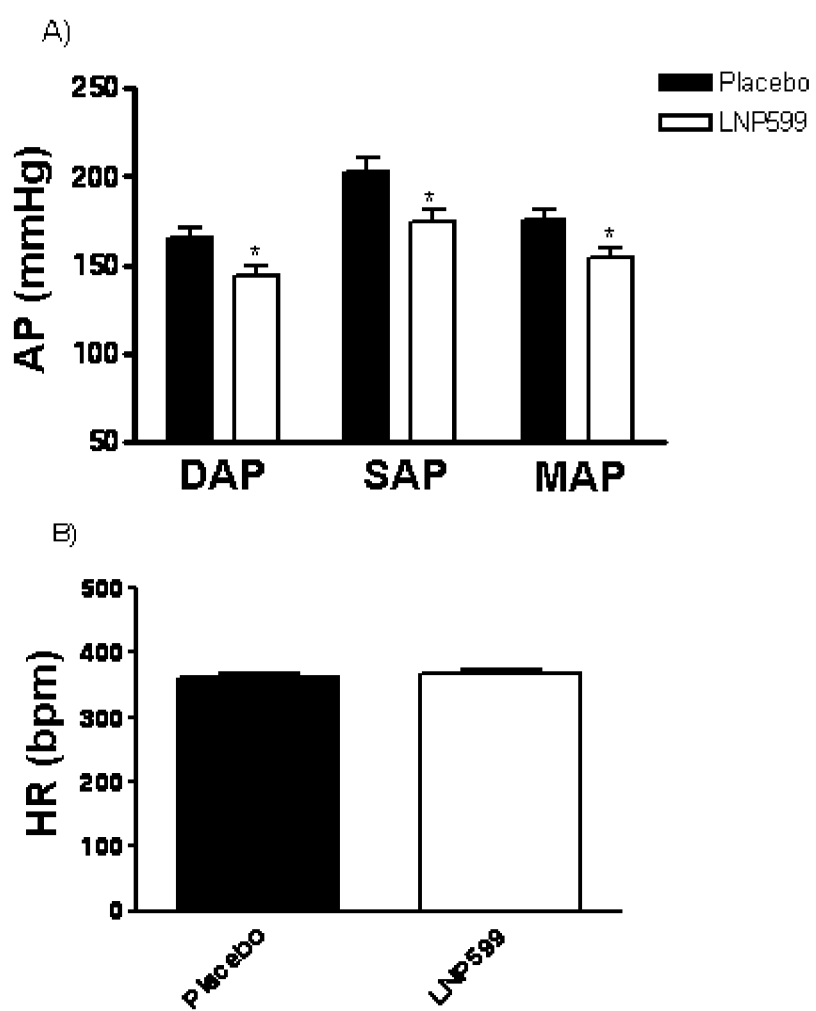

FIGS. 6A and 6B show the effects of 12-week treatment with compound 1 (20 mg/kg/d in drinking water) on arterial pressure (FIG. 6A) and heart rate (FIG. 6B) in SHHF rats measured conforming to Example 5.

At the end of treatment, the SHHF rats were anesthetized with sodium pentobarbital (50 mg/jg/i.p.), tracheotomies and ventilated with ambient air.

Arterial pressure and heart rate were recorded by means of a catheter inserted into the left femoral artery.

FIG. 6A: Y-axis: Arterial pressure in mm Hg; from left to right: diastolic arterial pressure (DAP), systolic arterial pressure (SAP) and mean arterial pressure (MAP). The histograms in black represent the control group, the white histograms represent the group treated with compound 1. *: $p<0.05$ (Student's t-test).

FIG. 6B: Y-axis: heart rate (HR) expressed in beats per minute (bpm): the black histogram represents the control group, the white histogram represents the group treated with compound 1.

Figure 7:
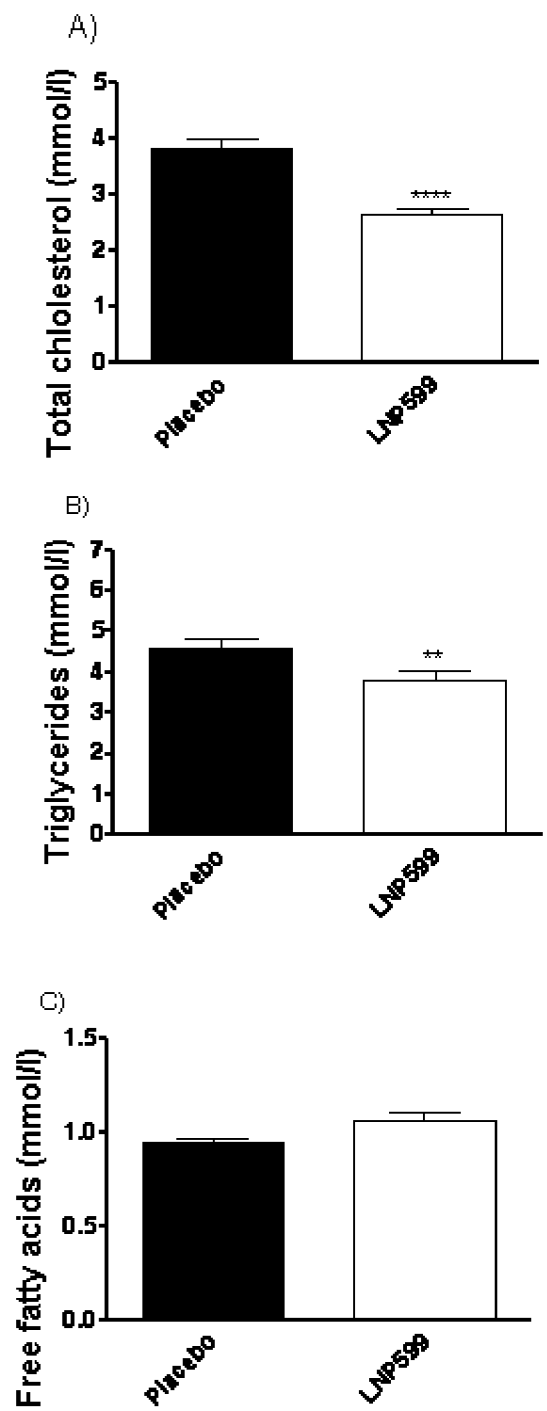

FIGS. 7A to 7C show the effects of 12-week treatment with compound 1 (20 mg/kg/d in drinking water) on total plasma cholesterol (FIG. 7A), triglycerides (FIG. 7B) and free fatty acids (FIG. 7C) in the plasma of SHHF rats, measured conforming to Example 5.

At the end of treatment the SHHF rats were anesthetized with isoflurane (2.5%) after a fasting time of 18 h and blood samples were obtained from the caudal vein.

FIG. 7A: Y-axis: total cholesterol (mmol/l); black histogram: control group; white histogram: group treated with compound 1. ****: $p<0.0001$ (Student's t-test).

FIG. 7B: Y-axis: triglycerides (mmol/l); black histogram: control group; white histogram: group treated with compound 1. **: $p<0.01$.

FIG. 7C: Y-axis: free fatty acids (mmol/l); black histogram: control group; white histogram: group treated with compound 1.

FIGS. 8A to 8G show the effects of 12-week treatment with compound 1 (20 mg/kg/d in drinking water) on the glucose metabolism in SHHF rats, measured conforming to Example 5.

At the end of treatment, the SHHF rats were anesthetized with sodium pentobarbital (50 mg/kg i.p.) after a fasting time of 18 h. The left femoral vein was catheterized to take blood samples for the different dosages. To perform the glucose tolerance test a solution of glucose (0.5 g/kg, i.v.) was administered and the plasma concentrations of glucose were determined after 3, 6, 10, 15, 30 and 45 minutes.

Figure 8:
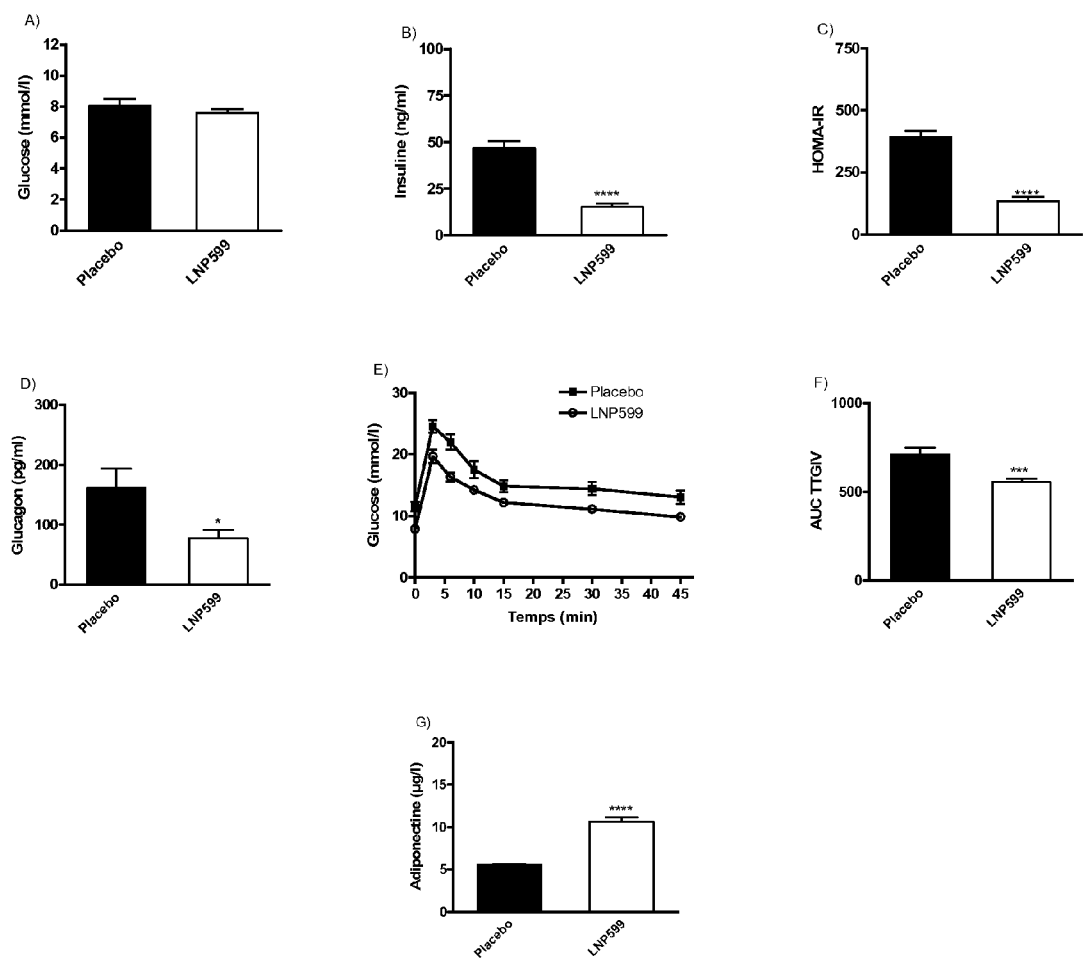

FIG. 8A: Y-axis: glucose (mmol/l); black histogram: control group; white histogram: group treated with compound 1.

FIG. 8B: Y-axis: insulin (ng/ml); black histogram: control group; white histogram: group treated with compound 1. ****: $p<0.0001$ (Student's t-test).

FIG. 8C: Y-axis (HOMA insulin-resistance index); black histogram: control group; white histogram: group treated with compound 1. ****: $p<0.0001$ (Student's t-test).

FIG. 8D: Y-axis: glucagon; black histogram: control group; white histogram: group treated with compound 1. *: $p<0.05$ (Student's t-test).

FIG. 8E: Y-axis: adiponectin (μg/ml); black histogram: control group; white histogram: group treated with compound 1. ****: $p<0.0001$ (Student's t-test).

FIG. 8F: Y-axis: time in minutes (black squares: control group; white circles: group treated with compound 1).

FIG. 8G: Y-axis: Area under curve (AUC) after the glucose tolerance test; black histogram: control group; white histogram: group treated with compound 1. ***: p<0.001 (Student's t-test).

FIG. 9 gives the pharmacological effects of compounds I-27 of the invention on mean arterial pressure (MAP) and on heart rate (HR) in anesthetized normotensive rats, measured conforming to Example 6.

PHARMACOLOGICAL PART

Example 1

In Vitro Experiments 1.1 Cell culture

3T3-L1 murine preadipocytes were cultured to confluence at 37° C. in DMEM medium containing 4.5 g/litre of D-glucose, 10% FCS and antibiotics. At confluence, differentiation of the 3T3-L1 adipocytes was initiated through the addition over 48 h of a mixture containing 100 µM methyl-isobutylxanthine, 100 nm dexamethasone and 175 nM insulin. The cells were then passaged every 2-3 days in DMEM, 10% FCS and 175 nM insulin. More than 95% of cells had the phenotype of mature adipocytes 10 days after confluence was reached.

The PC-12 cells were cultured in 75-cm$^2$ dishes in DMEM medium (1000 mg/l glucose) supplemented with 10% FBS inactivated by treatment at 56° C., 100 U/ml penicillin and 100 µg/ml streptomycin. When the cells reached confluence (3 to 4 days after the start of culture) they were harvested and passaged via the action of 0.25% trypsin for 2 minutes at 37° C. For the specific binding assays, the medium was removed and the cells stored by freezing to −20° C. until use with the membrane preparation.

1.2 Membrane Preparations and Cell Extracts

The adipocytes were washed twice with ice-cold PBS, harvested and homogenized in 25 mM Tris-HCl buffer, pH 7.5, 1 mM EDTA. The homogenates were centrifuged at 20,000×g for 15 min at 4° C. and the supernatant stored at −80° C. until use. The residues were re-suspended in 25 mM Tris-HCl buffer, pH 7.5, 1 mM EDTA and stored at −80° C. Aliquots of the homogenates and supernatants were used to determine the protein content (BC Assay Uptima Kit, Interchim, Montluçon, France) using BSA protein as standard.

The frozen PC12 cells were recovered by scraping in ice-cold Tris-HEPES buffer (5 mM Tris-HEPES, pH 7.7, 0.5 mM EDTA, 0.5 mM EGTA and 0.5 mM MgCl$_2$) and Potter homogenized. After centrifuging at 75,000 g for 20 min, the residue was washed in ice-cold Tris-HEPES buffer then again centrifuged. This last operation was performed twice. The residues were re-suspended in the same buffer at a concentration of 1 to 2 mg of proteins/ml. The membrane preparations were stored at −80° C. until use.

1.3 Binding Assay with Compound 1 on Membrane Preparations of Adipocytes and PC12 cells.

1.3.1. Operating Mode

The specific competitive binding assays were conducted using 0.5 nM [$^{125}$I]-PIC in the presence of 10 µM rauwolscine for the membranes of 3T3 cells, or in the absence of rauwolscine for the membranes of P12 cells, with 6 different concentrations of the ligand to be assayed, from 10$^{-9}$ to 10$^{-4}$ M.

Incubation was initiated through the addition of 3T3 cell membranes (10-26 µg proteins) or PC12 cell membranes (10-25 g proteins) in a final volume of 250 µl of Tris-HEPES buffer (50 mM Tris-HEPES, pH 7.7, 0.5 mM EDTA, 0.5 mM EGTA and 0.5 mM MgCl$_2$) and was performed at 25° C. for 45 min.

The reaction was halted by rapid vacuum filtration through GF/B fibre glass filters treated with 0.3% PEI using filtering equipment of Brandel® type, followed by three rapid washings of the filters using 3 ml of ice-cold 50 mM Tris-HCl buffer, pH 7.4. The radioactivity retained on the dried filters was determined using a Minaxi gamma counter (Packard, Meriden, CT, USA). Non-specific binding was determined by [$^{125}$I]PIC binding in the presence of 10 µM PIC and represented about 43% of total radioactivity. The choice of 10 µM PIC resulted from pilot experiments showing that at this concentration the residual binding obtained with PIC is similar to that obtained with clonidine.

1.3.2 Results

The results are given in FIG. 1.

The specific binding of 0.5 nM [$^{125}$I]-PIC was measured. It was between 2633 and 6652 cpm in the membrane preparation of 3T3 adipocytes, and between 2100 and 3400 cpm in the membrane preparation of PC12 cells.

In the (3T3) adipocyte membrane preparations, clonidine the reference molecule of IR$_1$ was capable of displacing specific binding of [$^{125}$I]-PIC in the preparation of 3T3 cell membranes with two affinities (IC$_{50}$=54.9±5.4 nM (57% of total sites) and 8144±426 nM, n=2) demonstrating the presence of the I$_1$ receptor in the preparation of 3T3-L1 membranes. In addition, selective compound 1 displaces the specific binding of [$^{125}$I]-PIC on the I$_1$ receptor onto a site of high affinity (IC$_{50}$=104±7 nM (n=4) (FIG. 1A)).

In the membrane preparations of PC12 cells, compound 1 selective for the I$_1$ receptor displaces specific binding of ($^{125}$I]-PIC with two affinities (high affinity IC$_{50}$=3.2±0.7 nM (55%) and low affinity 30698+5433 nM n=2) as shown in FIG. 1B.

The affinity for the α2-adrenergic receptor was assayed (see Table 1 under item 2.2). No significant displacement was observed at the concentration of 10$^{-5}$ M.

The affinities of compound 1 for more than 50 receptors and transporters were determined. Compound 1 does not exhibit any affinity similar to the affinity for the imidazoline receptor I$_1$ (FIG. 3).

1.4 Production of Adiponectin 1.4.1. Operating Mode

To determine the secretion of adiponectin by mature adipocytes, differentiated 3T3-L1 adipocytes (10 days after confluence) were placed in culture in 12-well plates and washed three times with DMEM, then cultured for 6 h in DMEM alone, in the absence or presence of 3 µM of compound 1. In some wells the antagonist selective for the imidazoline receptors I$_1$, efaroxan, was added (100 µM) 30 min before exposure to compound 1.

The culture medium was then recovered, centrifuged for 3 min at 10 000 g to remove cell contaminants, and the supernatant was stored at −80° C. until use. After two washings in cold PBS, the adipocytes were collected in PBS, homogenized and stored at −80° C. An aliquot of adipocyte homogenate was stored for protein determination. The adiponectin was measured using an ELISA kit following the manufacturer's recommendations. The adiponectin concentration was normalized with the cell protein content.

1.4.2 Results

Figure 2:
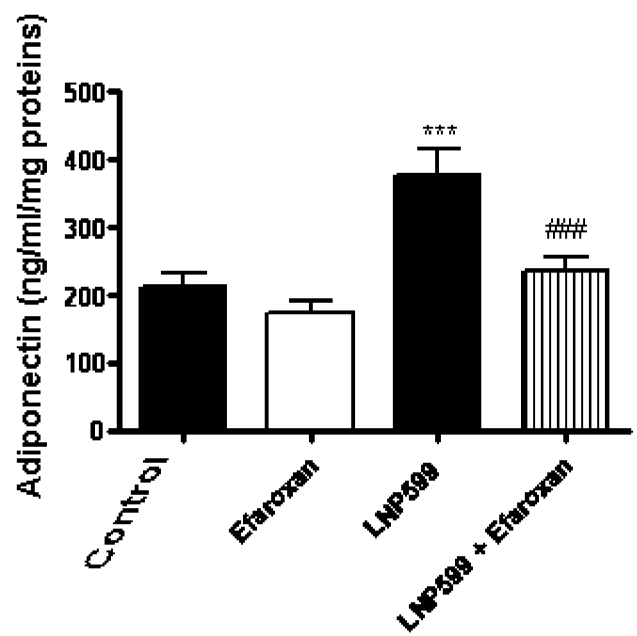
FIG. 2 illustrates the effect of compound 1 of the invention at a dose of 3 μmoles.1 on the secretion of adiponectin measured in the absence or presence of efaroxan at a dose of 100 μmoles/1 conforming to Example 1.4. ***$p<0.001$ compared with the control; ###$P<0.001$ compared with compound 1.

The results are given in FIG. 2.

Compound 1 at a dose of 3 µmol/l induced an increase in the secretion of adiponectin by the 3T3-L1 adipocytes (378±38 vs. 212.6±19.1 ng/ml/mg of proteins p<0.001). Pre-incubation with efaroxan, an antagonist selective for the I$_1$ receptors, at a dose of 100 µmol/l antagonizes the increase in adiponectin secretion (236±19.2 vs. 378±38 ng/ml/mg of proteins, p<0.001) whilst efaroxan alone at the same dose did not have any significant effect compared with the control (175.2±15.5 vs. 212.6±19.1 ng/ml/mg of proteins, p<0.05).

Example 2

Specific Binding Assay on Human Platelets 2.1 Operating Mode 2.1.1 Specific Binding Assay of the $I_1$ Receptor.

Binding assays were performed at 37° C. using [$^{125}$I]LNP 911 as radioligand following the general procedure described but adapted to washed whole platelets (Greney, H.; Urosevic, D.; Schann, S.; Dupuy, L.; Bruban, V.; Ehrhardt, J,-D.; Bousquet, P.; Dontenwill, M. [$^{125}$I]2-(2-Chloro-4-iodo-phenylamino)-5-methyl-pyrroline (LNP911), a High-Affinity Radioligand Selective for $I_1$ Imidazoline Receptors. *Mol. Pharmacol.* 2002, 62, 181-191).

Incubation was initiated through the addition of 900 to 950 µl of platelet suspension at a concentration of 500000/µl in a final volume of 1 ml Tyrode albumin and was performed at 37° C. for 5 min (equilibrium conditions). The competitive assays were conducted using a single concentration of radioligand (50 µM, 200 000 cpm), in the presence of increasing concentrations of suitable non-labelled ligand. Non-specific binding was determined by the binding of [$^{125}$I]LNP 911 in the presence of 100 nM of non-labelled LNP 911 and represented about 10% of total radioactivity when 50 µM of [$^{125}$I]LNP 911 were used.

The reaction was halted by rapid vacuum filtration through GF/C fibre glass filters followed by five rapid washings of the filters with 3 ml of ice-cold Tyrode (137 nM NaCl, 2.7 nM KCl, 12 nM NaHCO$_3$, 0.36 nM NaH$_2$PO$_4$, pH 7.35). Radioactivity was measured using a gamma counter (Wallac 1410).

2.1.2. Binding Assay of the $\alpha_2$-Adrenergic Receptors

The membrane preparation was prepared as described by Newman-Tancredi, A.; Nicolas, J,-P.; Audinot, V.; Gavaudan, S.; Verriele, L.; Touzard, M.; Chaput, C.; Richard, N.; Millan, N. J. (Action of alpha2 Adrenoreceptor Ligands at alpha2A and 5-HT1A Receptors: the Antagonist, Atipamezole, and the Agonist, Dexmedetomidine, are Highly Selective for alpha2A Adrenoreceptors. *Naunyn-Schmiedeberg's Arch. Pharmacol.* 1998, 358, 197-206).

These membranes (30 µg proteins/ml for CHO-h$\alpha_{2A}$ and CHO-h$\alpha_{2B}$, 100 µg protein/ml for CHO-h$\alpha_{2C}$) were incubated for 60 min at ambient temperature in binding buffer (33 mM Tris-HCl, 1 mM EDTA, pH 7.5) in a final volume of 500 µL containing 0.8 or 1 or 2 nM [$^3$H]RX821002 respectively for the adrenergic receptors h$\alpha_{2A}$, h$\alpha_{2B}$ and h$\alpha_{2C}$.

Incubation was halted by rapid vacuum filtration through GF/C glass fibre filters followed by three successive washings in ice-cold binding buffer.

Non-specific binding was determined using 10 µM phentolamine.

2.2 Results

The competitive assays were analyzed by non-linear regression using the GraphPad programme.

Ki values were determined using the method described by Cheng and Prussof (Cheng, Y. C.; Prusoff, W. H. Relationship between the Inhibition Constant (Ki) and the Concentration of Inhibitor which causes 50 percent Inhibition ($I_{50}$) of an Enzymatic Reaction. *Biochem. Pharmacol.* 1973, 22, 3099-3108).

The results are given in Table I below:

TABLE I

| Compounds | $I_1$ Ki (M)[#] | $\alpha_2$ Ki (M)[§] |
|---|---|---|
| 1 | $8.1 \times 10^{-9}$ | $>10^{-5}$ |
| 5 | $1.9 \times 10^{-8}$ | $>10^{-5}$ |
| 8 | $2.2 \times 10^{-10}$ | $>10^{-5}$ |
| 9 | $2.8 \times 10^{-9}$ | $>10^{-5}$ |
| 13 | $1.2 \times 10^{-7}$ | $>10^{-5}$ |
| 20 | $2.8 \times 10^{-9}$ | $>10^{-5}$ |

[#]measured on platelets with [$^{125}$I]LNP 911 except for compound 13 whose measurement was performed on PC12 cells with [$^{125}$I] PIC;
[§]measured on CHO cells with phentolamine.

The results given above clearly show the specificity of the compounds of the invention for the imidazoline receptor of type 1 compared with the $\alpha_2$-adrenergic receptors.

Example 3

Specific Binding Assay of Compound 1 on Different Receptors, Transporters and Enzymes 3.1 Operating Mode Compound 1 was assayed at two concentrations $10^{-7}$ (1.0E-07) M and $10^5$ (1.0E-05) on different receptors, transporters and enzymes using the techniques described in the literature and adapted for the laboratory.

3.2 Results

These are given in the table in FIG. 3.

The results given above clearly show that compound 1 does not bind to any of the assayed receptors, transporters and enzymes with affinity similar to the affinity of compound 1 for the IR$_1$ receptors.

Example 4

Measurement of Renal Sympathetic Nerve Activity (RSNA): Effect of Acute Treatment with Compound 1 at 10 mg/kg (i.v.) on Hemodynamic Parameters and Sympathetic Activity 4.1 Operating Mode Male Sprague-Dawley rats (10 weeks; Laboratoires Charles River, L'Arbresle, France) were anesthetized with urethane (1.5 g/kg i.p., supplemented with 0.1 g/kg i.v. if necessary) and placed on a hot blanket to maintain rectal temperature at 37° C. Catheters were inserted into the lower abdominal aorta and inferior vena cava for measurement of arterial pressure and administration of the compound respectively.

The left renal nerve was carefully isolated and a major branch of the nerve was placed on a bipolar platinum-iridium electrode insulated with silicone gel (604A and B; Wacker Chemie, Munich, Germany). Throughout the experiment the rat was ventilated by means of a tracheal cannula (7-8 ml/kg× 72 cycles/min) with a mixture of oxygen and air (~8%-20%).

Arterial pressure was measured by connecting the arterial catheter to a pressure transducer (TNF-R; Ohmeda, Bilthoven, Holland) coupled to an amplifier (model 13-4615-52; Gould, Cleveland, Ohio).

Renal sympathetic nerve activity (RSNA) was amplified (×50,000), the pass-band filtered (300-3000 Hz; Model P-511J; Grass, Quincy, Mass.) and rectified with a home-built analogue rectifier including a low frequency filter with a cut-off frequency of 150 Hz.

The 2 parameters were continuously recorded using a computer equipped with an analogue-digital converter (model AT-MIO-16; National Instruments, Austin, Tex.) and LabVIEW 5.1 software (National Instruments).

Arterial pressure and RSNA were recorded before (baseline) and after administering compound 1 (10 mg/kg, i.v.). At the end of the recording session, chlorisondamine, a ganglionic blocker, was administered (2.5 mg/kg, i.v.) to evaluate the level of background noise which was then subtracted from all RSNA data for subsequent analyses. At the end of the experiment, the rats were euthanized with an intravenous overdose of sodium pentobarbital.

4.2 Results

The results are given in FIGS. 4A to 4C.

Compound 1, at a dose of 10 mg/kg, i.v., causes a 50% reduction in renal sympathetic activity (FIG. 4A).

In parallel, compound 1 at the same concentration causes a strong reduction in arterial pressure (SAP: $105.3 \pm 3$ vs. $141.7 \pm 2.3$ mmHg, $p<0.001$; MAP: $77.4 \pm 3.6$ vs. $108. \pm 3.4$ mmHg, $p<0.0001$; DAP: $58.6 \pm 3.4$ vs. $83.2 \pm 4$ mmHg, $p>0.001$) and in heart rate ($288.4 \pm 10.3$ vs $331.4 \pm 14$ bpm, $p>0.01$) (FIGS. 4B and 4C). The reduction in renal sympathetic activity, in arterial pressure and in heart rate lasted more than one hour.

Example 5

Measurement of Arterial Pressure, of Heart Rate, of Plasma Biochemical Parameters and Glucose Metabolism: Effect of Chronic Treatment with Compound 1 at a Dose of 20 mg/kg/d per os for 12 Weeks 5.1. Operating Mode
5.1.1 Animals Male SHHF rats (spontaneously hypertensive, heart failure) aged 12 weeks were used for this study (Charles River breeding centre, L'Arbresle, France).

The animals were placed in a room with controlled temperature and light, had free access to tap water and were fed a standard diet (A04, SAFE, Augy, France). This study was conducted in agreement with institutional recommendations and the rules laid down by the European Community for the use of experimental animals (L358-86/609/EEC).

5.1.2 Chronic Treatment with Compound 1

Compound 1 was administered in the drinking water for 12 weeks at a dose of 20 mg/kg/d (n=17). Water consumption was regularly measured to adjust the concentration of compound 1. Non-treated control SHHF rats had access to normal water (n=10).

Body weight, water and food intake were measured every day. After a treatment time of 12 weeks, blood samples were taken. Three days later, arterial pressure and heart rate were recorded and a glucose tolerance test was performed.

5.1.3 Recording of Arterial Pressure and Heart Rate

The rats were anesthetized with pentobarbital 50 mg/kg, i.p. (Céa santé animale, Libourne, France) and tracheotomized. The femoral vein and artery were catheterized for administration of the substances and measurement of arterial pressure respectively. The rats were ventilated with ambient air and paralyzed through the administration of pancuronium bromide (1.5 mg/kg, iv; Organon SA, France). Arterial pressure was recorded after stabilization with a pressure transducer (Gould P23XL) and recorder (Gould Electronics BS 272, Longjumeau, France). Mean arterial pressure (MAP) was calculated as diastolic pressure plus one third of differential arterial pressure. Heart rate was also recorded from the pressure signal using a Gould Biotach amplifier (model 13-4615-66).

The results are given in FIGS. 6A and 6B.

After a treatment time of 12 weeks at the dose of 20 mg/kg/d with compound 1 in drinking water, the arterial pressure of the SHHF rats showed a significant decrease ($153 \pm 7$ vs. $176 \pm 6$ mmHg, $p>0.05$) (FIG. 6A) but there was no change in heart rate ($367 \pm 6$ vs. $361 \pm 8$ bpm, $p>0.05$) (FIG. 6B).

5.1.4 Measurement of Plasma Biochemical Parameters

After a treatment time of 12 weeks, blood samples were obtained from the caudal vein of anesthetized rats (2.5% isoflurane, Abbott, Rungis, France) after a fasting time of 18 h.

The blood were centrifuged for 15 minutes at 2000 g and the plasma was frozen to $-80°$ C. until assays of glucose, total cholesterol, HDL and LDL cholesterol and fatty acids. These assays were performed at the following centre: Plateau Technique Biologique des Hôpitaux Universitaires de Strasbourg (Advia 2400, Bayer HealthCare).

Insulin, leptin, adiponectin and glucagon were assayed using ELISA kits (insulin: Mercodia, Uppsala, Sweden; leptin: Yanaihara Institute Inc., Shizuoka, Japan; adiponectin: B-Bridge International, Mountain View, USA; glucagon: Gentaur, Kampenhout, Belgium) following the supplier's recommendations.

The results are given in FIGS. 7A to 7C and FIGS. 8A to 8E.

After a treatment period of 12 weeks with compound 1, a major decrease in total plasma cholesterol was observed ($2.7 \pm 0.09$ vs. $3.8 \pm 0.18$ mmol/l, $p<0.0001$) (FIG. 7A). Compound 1 also caused a drop in the concentration of plasma triglycerides ($3.8 \pm 0.25$ vs. $4.59 \pm 0.23$ mmol/l, $p<0.01$) (FIG. 7B); free fatty acids were not affected by the treatment (FIG. 7C).

Fasting glycaemia was not affected by the treatment (FIG. 8A) but fasting plasma insulin was significantly reduced ($15.2 \pm 2$ vs. $46.8 \pm 3.7$ ng/ml, $p<0.0001$) (FIG. 8B).

Calculation of the HOMA-IR index confirmed that the treated SHHF rats had improved sensitivity to insulin compared with the control SHHF rats ($110 \pm 14$ vs. $534 \pm 38$, $p<0.0001$) (FIG. 8C). Finally, compound 1 caused a significant drop in glucagon ($77.3 \pm 14$ vs. $161.3 \pm 33$ µg/ml, $p<0.05$) (FIG. 6D) and a strong increase in the concentration of plasma adiponectin ($10.6 \pm 0.52$ vs. $5.54 \pm 0.14$ µg/l, $p<0.0001$) (FIG. 8E).

5.1.5 Glucose Tolerance Test (IVGTT)

A glucose solution of 0.5 g/kg was administered via intravenous route. The plasma concentration of glucose was evaluated using a glucometer before injection into animals that had fasted 18 h, and then 3, 6, 10, 15, 30 and 45 min after administration of the glucose (Accu Check Go, Roche Diagnostics, Meylan, France). Area under curve values (AUC) were then determined to compare the groups.

5.2 Results 5.2.1 Measurement of Body Weight and Food Consumption

Results on weight and food consumption are given in FIGS. 5A and 5B.

After a treatment time of 9 weeks and up until the end of treatment, the SHHF rats treated with compound 1 showed a lower body weight than the controls; their food consumption was already below that of the controls after one week's treatment (FIGS. 5A and 5B).

5.2.2 Measurement of Plasma Biochemical Parameters

The results are given in FIGS. 7A to 7C and FIGS. 8A to 8E.

After 12 weeks' treatment with compound 1a strong decrease in total plasma cholesterol was observed (2.7±0.09 vs. 3.8±0.18 mmol/l, p<0.0001) (FIG. 7A).

Compound 1 also caused a drop in the concentration of plasma triglycerides (3.8±0.25 vs. 4.59±0.23 mmol/l, p<0.01 (FIG. 7B); free fatty acids were not affected by the treatment (FIG. 7C).

Fasting glycaemia was not affected by the treatment (FIG. 8A) but fasting plasma insulin was significantly reduced (15.2±2 vs. 46.8±3.7 ng/ml, p<0.0001) (FIG. 8B).

Calculation of the HOMA-IR index confirmed that the treated SHHF rats were more sensitive to insulin than the control SHHF rats (110±14 vs. 534±38, p<0.0001) (FIG. 8C). Finally, compound 1 caused a significant drop in glucagon (77.3±14 vs. 161.3±33 g/ml, p<0.05) (FIG. 6D) and a strong increase in the concentration of plasma adiponectin (10.6±0.52 vs. 5.54±0.14 µg/l, p<0.0001) (FIG. 8E).

5.2.3 Glucose Tolerance Test (IVGTT)

The results are given in FIGS. 8F and 8G.

Compound 1 increased glucose tolerance in SHHF rats (AUC: 556±20 s. 710±37 mmol·min/l, p<0.001) (FIGS. 8F and 8G).

Example 6

Measurement of Arterial Pressure and Heart Rate: Effect of Acute Treatment Via Intravenous or Intracisternal Route 6.1 Operating Mode Adult, male Wistar rats were anesthetized with pentobarbital 50 mg/kg, i.p., and their physiological temperature was held constant. The animals were tracheotomized and the left carotid was catheterized to allow i.v. administration. The animals were paralyzed through the administration of pancuronium bromide (1 mg/kg, i.v.; Organon SA, France) and ventilated with ambient air (Hugo Sachs electronic model 7025). A catheter was inserted into the left femoral artery and connected to a pressure transducer and recorder (Gould electronics BS 272, Longjumeau, France). Heart rate, systolic arterial pressure, diastolic arterial pressure and mean arterial pressure (MAP) were continuously recorded from the pressure signal (Gould Biotach amplifier model 13-4615-66); [MAP=DAP+⅓ (SAP-DAP)]. The mean arterial pressure (MAP) and heart rate (HR) were measured for 90 minutes.

6.2 Results

The results are expressed as the maximum variation in mean arterial pressure expressed in mm of mercury (mmHg), and heart rate is expressed in beats per minute (bpm) compared with baseline values before treatment. The corresponding percentage variation was also determined. The results are considered significant when variation is 10% higher than the baseline value.

In the experiments in which the drug was injected via intracisternal route, 0.2 ml of a drug solution was injected after withdrawing an identical volume of cerebrospinal fluid.

The results are given in the table in FIG. 9.

The invention claimed is:

1. A compound of following general formula (I):

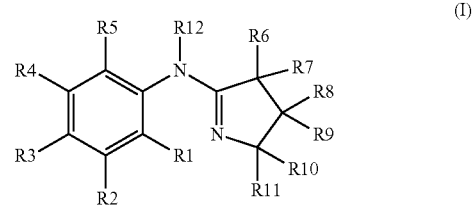

wherein:
a) R12 represents H, and
R1 and R2 each independently are:
a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, $CO_2H$, $CO_2R'$ where R' is a straight-chain or branched C1-C8 alkyl or C3-C6 cycloalkyl; or
R1 and R2 together form a C5 ring;
R3, R4 and R5 each independently represent:
a hydrogen, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, a C1-C5 perfluoroalkyl, C1-C8 acyl, OH, SH, a primary, secondary or tertiary amine, CN, $CO_2H$, $CO_2R'$ where R' is a straight-chain or branched C1-C8 alkyl, or a C3-C6 cycloalkyl;
R6, R7, R9 and R11 represent hydrogens; and
R8 and R10 are selected from the group consisting of a hydrogen and straight-chain or branched C1 to C5 alkyl, at least one of the two being a straight-chain or branched C1 to C5 alkyl; or
b) R12 represents $CH(R13)(CH_2)$ and forms a C5 ring with R5, R13 representing H or $CH_3$,
R1, R2, R3 and R4 are selected from the group consisting of a hydrogen, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, a C1-C5 perfluoroalkyl, C1-C8 acyl, —OH, —SH, a primary, secondary or tertiary amine, —CH, —$CO_2H$, —$CO_2R'$ where R' is a straight-chain or branched C1-C8 alkyl, and a C3-C6 cycloalkyl;
R6, R7, R9 and R11 represent hydrogens; and
R8 and R10 are selected from the group consisting of a hydrogen and straight-chain or branched C1 to C5 alkyl, at least one of the two being a straight-chain or branched C1 to C5 alkyl,
provided that at least one substituent selected from R1 and R13 is not a hydrogen; and
pharmacologically acceptable salts thereof.

2. The compound according to claim 1 of following general formula (Ia):

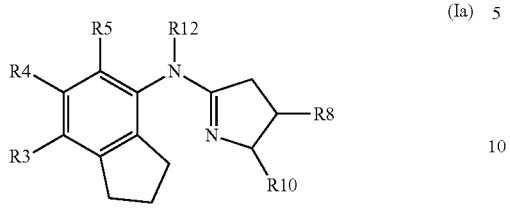

where:

R3 and R12 are hydrogens;

R8 and R10 are selected from the group consisting of a hydrogen and straight-chain or branched C1 to C5 alkyl, at least one of the two being a straight-chain or branched C1 to C5 alkyl; and R4 and R5 are independently selected from the group consisting of a hydrogen, halogen, straight-chain or branched C1 to C3 alkyl, straight-chain or branched C1 to C3 alkoxy, C1-C3 perfluoroalkyl, C1-C3 acyl, OH, SH, a primary, secondary or tertiary amine, CN, $CO_2H$ and $CO_2R'$ where R' is a straight-chain or branched C1-C3 alkyl.

3. The compound according to claim 2, wherein R4 and R5 are hydrogens.

4. The compound according to claim 1 of following general formula (Ib):

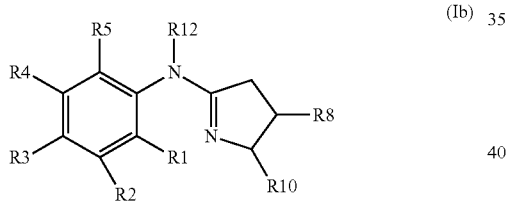

where:

R12 is a hydrogen;

R8 and R10 are selected from the group consisting of a hydrogen and straight-chain or branched C1 to C5 alkyl, at least one of the two being a straight-chain or branched C1 to C5 alkyl;

R1 and R2 are independently selected from the group consisting of a halogen, straight-chain or branched C1 to C3 alkyl, straight-chain or branched C1 to C3 alkoxy, C1-C3 perfluoroalkyl and a C1-C3 acyl; and R3, R4 and R5 are independently selected from the group consisting of a hydrogen, halogen, straight-chain or branched C1 to C3 alkyl, straight-chain or branched C1 to C3 alkoxy, C1-C3 perfluoroalkyl, C1-C3 acyl, OH, SH a primary, secondary or tertiary amine, CN, $CO_2H$ and $CO_2R'$ where R' is a straight-chain or branched C1-C3 alkyl.

5. The compound according to claim 4, wherein R3, R4 and R5 are hydrogens.

6. The compound according to claim 4, wherein R1 and R2 are independently selected from the group consisting of a halogen and straight-chain or branched C1 to C3 alkyl.

7. A compound selected from formulae 1-2 and 4-7:

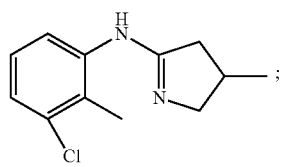

1

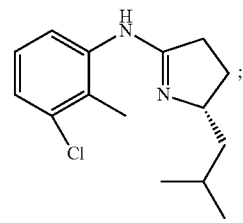

2

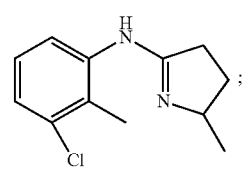

4

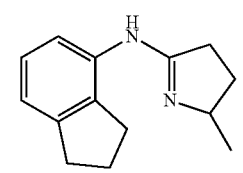

5

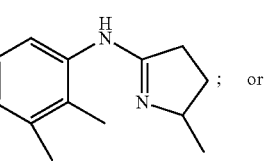

6

; or

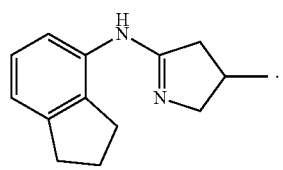

7

.

8. The compound according to claim 1 of following formula (Ic):

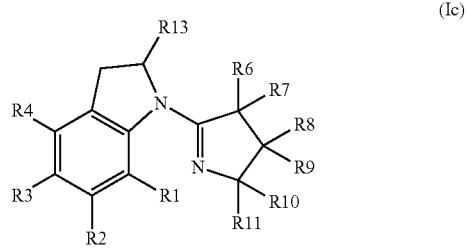

(Ic)

where:

R1, R2, R3 and R4 are selected from the group consisting of a hydrogen, halogen, straight-chain or branched C1 to C3 alkyl, straight-chain or branched C1 to C3 alkoxy, C1-C3 perfluoroalkyl, C1-C3 acyl, OH, SH, a primary, secondary or tertiary amine, —CN, —CO₂H and —CO₂R' where R' is a straight-chain or branched C1-C3 alkyl; and R8 and R10 are selected from the group consisting of a hydrogen and straight-chain or branched C1 to C5 alkyl, at least one of the two being a straight-chain or branched C1 to C5 alkyl, provided that at least one substituent selected from R1 and R13 is not a hydrogen.

9. The compound according to claim 8, wherein:
R2, R3, R4 are hydrogens,
R13 is H and R1 is a halogen and straight-chain or branched C1 to C3 alkyl; or
R13 is a methyl and R1 is selected from the group consisting of a hydrogen, halogen and straight-chain or branched C1 to C3 alkyl; and
R8 and R10 are selected from the group consisting of a hydrogen and straight-chain or branched C1 to C5 alkyl, at least one of the two being a straight-chain or branched C1 to C5 alkyl.

10. The compound according to claim 8 selected from one of the following formulas:

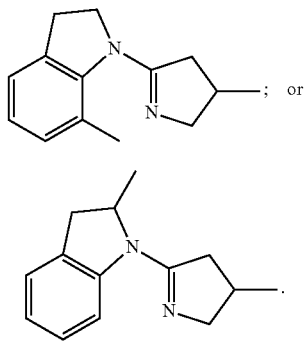

11. The compound according to claim 2, wherein R4 and R5 are independently selected from the group consisting of a halogen, straight-chain or branched C1 to C3 alkyl, straight-chain or branched C1 to C3 alkoxy, C1-C3 perfluoroalkyl and a C1-C3 acyl.

12. The compound according to claim 4, wherein R3, R4 and R5 are independently selected from the group consisting of a halogen, straight-chain or branched C1 to C3 alkyl, straight-chain or branched C1 to C3 alkoxy, C1-C3 perfluoroalkyl and a C1-C3 acyl.

13. A pharmaceutical composition comprising as active ingredient at least one compound according to claim 1 in association with a pharmaceutically acceptable vehicle.

14. The pharmaceutical composition according to claim 13, wherein said composition is suitable for oral administration.

15. The pharmaceutical composition according to claim 14, wherein the dose of the active ingredient is between 1 mg/kg and 100 mg/kg in man.

16. A method for treating metabolic syndrome by administering to a patient in need thereof a pharmaceutical composition containing as active ingredient at least one compound according to claim 1, in association with a pharmaceutically acceptable vehicle, at an effective dose.

17. The method according to claim 16, wherein said pharmaceutical composition is administered orally.

18. The compound of claim 1, wherein:
R 12 represents H, and
R1 and R2 each independently are:
a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, C1-C5 perfluoroalkyl, C1-C8 acyl, OH, SH, a primary, secondary or tertiary amine, CN, CO₂H, CO₂R' where R' is a straight-chain or branched C1-C8 alkyl or C3-C6 cycloalkyl; or
R1 and R2 together form a C5 ring;
R3, R4 and R5 each independently represent:
a hydrogen, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, a C1-C5 perfluoroalkyl, C1-C8 acyl, OH, SH, a primary, secondary or tertiary amine, CN, CO₂H, CO₂R' where R' is a straight-chain or branched C1-C8 alkyl, or a C3-C6 cycloalkyl;
R6, R7, R9 and R11 represent hydrogens; and
pharmacologically acceptable salts thereof.

19. The compound of claim 1, wherein:
R12 represents CH(R13)(CH₂) and forms a C5 ring with R5, R13 represents H or CH₃,
R1, R2, R3 and R4 are selected from the group consisting of a hydrogen, a halogen, straight-chain or branched C1 to C8 alkyl, C2-C8 alkene, straight-chain or branched C1 to C8 alkoxy, C3-C6 cycloalkyl, C5-C6 bicycloalkyl, a polyether chain, a C1-C5 perfluoroalkyl, C1-C8 acyl, —OH, —SH, a primary, secondary or tertiary amine, —CH, —CO₂H —CO₂R' where R' is a straight-chain or branched C1-C8 alkyl, and a C3-C6 cycloalkyl;
R6, R7, R9 and R11 represent hydrogens; and
R8 and R10 are selected from the group consisting of a hydrogen and straight-chain or branched C1 to C5 alkyl, at least one of the two being a straight-chain or branched C1 to C5 alkyl,
provided that at least one substituent selected from R1 and R13 is not a hydrogen; and pharmacologically acceptable salts thereof.

* * * * *